(12) United States Patent
Hall et al.

(10) Patent No.: US 6,196,230 B1
(45) Date of Patent: Mar. 6, 2001

(54) STENT DELIVERY SYSTEM AND METHOD OF USE

(75) Inventors: Todd A. Hall, Goshen; Greg R. Furnish; Simon M. Furnish, both of Louisville, all of KY (US); Scott J. Wolf, Minneapolis, MN (US); Peter J. Wilk, New York, NY (US); David Y. Phelps, Louisville, KY (US); Vincent Pompili, Carmel, IN (US)

(73) Assignee: Percardia, Inc., Nashua, NH (US)

( * ) Notice: Subject to any disclaimer, the term of this patent is extended or adjusted under 35 U.S.C. 154(b) by 0 days.

(21) Appl. No.: 09/150,181

(22) Filed: Sep. 10, 1998

(51) Int. Cl.[7] ................................. A61B 19/00

(52) U.S. Cl. ................ 128/898; 606/108; 606/194

(58) Field of Search .................... 606/198, 194, 606/195, 1, 108, 200; 623/1, 12; 604/96; 600/16; 128/898

(56) References Cited

U.S. PATENT DOCUMENTS

| | | |
|---|---|---|
| 3,042,021 | 7/1962 | Read . |
| 3,419,010 | 12/1968 | Williamson . |
| 3,882,862 | 5/1975 | Berend . |
| 3,911,502 | 10/1975 | Boretos . |
| 4,474,569 | 10/1984 | Newkirk . |

(List continued on next page.)

FOREIGN PATENT DOCUMENTS

| | | |
|---|---|---|
| 0 732 088 | 9/1996 | (EP) . |
| 0 834 287 | 4/1998 | (EP) . |
| 0 876 803 | 11/1998 | (EP) . |
| 0 904 745 | 3/1999 | (EP) . |
| 0 955 017 | 11/1999 | (EP) . |

(List continued on next page.)

OTHER PUBLICATIONS

Gardner, M.D. et al., "An Experimental Anatomic Study of Indirect Myocardial Revascularization," *Journal of Surgical Research*, May 1971, vol. 11, No. 5, pp. 243–247.

Palmaz et al., "Expandable Intrahepatic Portacaval Shunt Stents: Early Experience in the Dog," *AJR*, 1985, vol. 145, pp. 821–825.

Palmaz et al., "Expandable Intrahepatic Portacaval Shunt Stents in Dogs with Chronic Portal Hypertension," *AJR*, 1986, vol. 147, pp. 1251–1254.

(List continued on next page.)

*Primary Examiner*—Pedro Philogene
(74) *Attorney, Agent, or Firm*—Finnegan, Henderson, Farabow, Garrett & Dunner, L.L.P.

(57) ABSTRACT

Described herein are various methods and apparatuses for delivering stents and other devices into the myocardium of a patient. One preferred stent delivery system provides access to the insertion site in the myocardium by advancing a delivery catheter through a blockage in a coronary artery, or around the blockage through a coronary vein or through a channel or tunnel formed around the blockage. In one embodiment, once the distal end of the delivery catheter is adjacent the myocardium, an angled bend is created in the catheter by actuating expandable steering guides mounted to the catheter which cooperate with the walls of the blood vessel to cause the catheter to turn. Then, a guidewire is advanced through the delivery catheter and into the myocardium. In another embodiment, a tip-deflecting pull wire extends from the distal end of the delivery catheter which may be actuated to turn towards and then inserted into the myocardium. In another embodiment, an exit port facing the insertion site is provided within the catheter or a balloon mounted on the catheter so that a guidewire may be directed through a lumen and out the exit port into the myocardium. Once the guidewire punctures into the myocardium, the guidewire is anchored using barbs, balloons or other actuatable members to secure the guidewire to the myocardium. Subsequently, using a push-pull mechanism, stents and other medical devices can be advanced over the guidewire into the myocardium.

38 Claims, 34 Drawing Sheets

U.S. PATENT DOCUMENTS

| | | |
|---|---|---|
| 4,531,936 | 7/1985 | Gordon . |
| 4,540,402 | 9/1985 | Aigner . |
| 4,655,773 | 4/1987 | Grassi . |
| 4,733,665 | 3/1988 | Palmaz . |
| 4,790,810 | 12/1988 | Pugh et al. . |
| 4,836,204 | 6/1989 | Landymore et al. . |
| 4,955,856 | 9/1990 | Phillips . |
| 4,973,301 | 11/1990 | Nissenkorn . |
| 4,979,955 | 12/1990 | Smith . |
| 5,000,734 | 3/1991 | Boussignac et al. . |
| 5,052,998 | 10/1991 | Zimmon . |
| 5,176,626 | 1/1993 | Soehendra . |
| 5,183,464 | 2/1993 | Dubrul et al. . |
| 5,190,058 | 3/1993 | Jones et al. . |
| 5,226,889 | 7/1993 | Sheiban . |
| 5,258,008 | 11/1993 | Wilk . |
| 5,287,861 * | 2/1994 | Wilk .................................. 128/898 |
| 5,327,913 | 7/1994 | Taheri . |
| 5,330,486 | 7/1994 | Wilk . |
| 5,344,426 | 9/1994 | Lau et al. . |
| 5,386,818 | 2/1995 | Schneebaum et al. . |
| 5,409,019 | 4/1995 | Wilk . |
| 5,429,144 * | 7/1995 | Wilk .................................. 128/898 |
| 5,456,694 | 10/1995 | Marin et al. . |
| 5,462,544 | 10/1995 | Saksena et al. . |
| 5,470,320 | 11/1995 | Tifenbrun et al. . |
| 5,487,760 | 1/1996 | Villafana . |
| 5,554,119 | 9/1996 | Harrison et al. . |
| 5,593,434 | 1/1997 | Williams . |
| 5,643,278 | 7/1997 | Wijay . |
| 5,655,548 | 8/1997 | Nelson et al. . |
| 5,662,124 | 9/1997 | Wilk . |
| 5,676,434 | 10/1997 | Kim . |
| 5,676,670 | 10/1997 | Kim . |
| 5,683,447 | 11/1997 | Bush et al. . |
| 5,713,950 | 2/1998 | Cox . |
| 5,722,972 | 3/1998 | Power et al. . |
| 5,733,267 | 3/1998 | Del Toro . |
| 5,755,682 | 5/1998 | Knudson et al. . |
| 5,758,663 | 6/1998 | Wilk et al. . |
| 5,797,920 | 8/1998 | Kim . |
| 5,810,836 | 9/1998 | Hussein et al. . |
| 5,810,871 | 9/1998 | Tuckey et al. . |
| 5,824,071 | 10/1998 | Nelson et al. . |
| 5,830,222 * | 11/1998 | Makower .......................... 606/159 |
| 5,851,232 | 12/1998 | Lois . |
| 5,865,723 | 2/1999 | Love . |
| 5,878,751 | 3/1999 | Hussein et al. . |
| 5,885,258 | 3/1999 | Sachdeva et al. . |
| 5,891,154 * | 4/1999 | Loeffler .......................... 606/108 |
| 5,908,028 | 1/1999 | Wilk . |
| 5,908,029 | 6/1999 | Knudson et al. . |
| 5,935,119 | 8/1999 | Guy et al. . |
| 5,944,019 | 8/1999 | Knudson et al. . |
| 5,948,191 * | 9/1999 | Solovay .......................... 606/192 |
| 5,971,993 | 10/1999 | Hussein et al. . |
| 5,976,153 | 11/1999 | Fischell et al. . |
| 5,976,155 | 11/1999 | Foreman et al. . |
| 5,976,178 | 11/1999 | Goldstein et al. . |
| 5,976,181 | 11/1999 | Whelan et al. . |
| 5,979,455 | 11/1999 | Maginot . |
| 5,980,530 | 11/1999 | Willard et al. . |
| 5,980,533 | 11/1999 | Holman . |
| 5,984,956 | 11/1999 | Tweden et al. . |
| 5,989,263 | 11/1999 | Shmulewitz . |
| 5,997,563 | 12/1999 | Kretzers . |
| 6,001,123 | 12/1999 | Lau . |
| 6,007,543 | 12/1999 | Ellis et al. . |
| 6,029,672 | 2/2000 | Vanney et al. . |
| 6,036,697 | 3/2000 | DiCaprio . |
| 6,039,721 | 3/2000 | Johnson et al. . |
| 6,042,581 | 3/2000 | Ryan et al. . |
| 6,053,924 | 4/2000 | Hussein . |
| 6,053,942 | 4/2000 | Eno et al. . |
| 6,068,638 | 5/2000 | Makower . |
| 6,071,292 | 6/2000 | Makower et al. . |
| 6,076,529 | 6/2000 | Vanney et al. . |

FOREIGN PATENT DOCUMENTS

| | | |
|---|---|---|
| 0 955 019 | 11/1999 | (EP) . |
| 0 962 194 | 12/1999 | (EP) . |
| 2 316 322 | 10/1998 | (GB) . |
| 93/15791 | 8/1993 | (WO) . |
| 94/16629 | 8/1994 | (WO) . |
| WO 96/39964 | 12/1996 | (WO) . |
| 97/13463 | 4/1997 | (WO) . |
| 97/13471 | 4/1997 | (WO) . |
| WO 97/13463 | 4/1997 | (WO) . |
| WO 97/13471 | 4/1997 | (WO) . |
| 97/27893 | 8/1997 | (WO) . |
| 97/27898 | 8/1997 | (WO) . |
| 97/32551 | 9/1997 | (WO) . |
| 97/41916 | 11/1997 | (WO) . |
| 98/06356 | 2/1998 | (WO) . |
| WO 98/06356 | 2/1998 | (WO) . |
| 98/08456 | 3/1998 | (WO) . |
| 98/10714 | 3/1998 | (WO) . |
| WO 98/08456 | 3/1998 | (WO) . |
| 98/16161 | 4/1998 | (WO) . |
| WO 98/16161 | 4/1998 | (WO) . |
| WO 98/38942 | 9/1998 | (WO) . |
| 98/46115 | 10/1998 | (WO) . |
| 98/46119 | 10/1998 | (WO) . |
| 98/49964 | 11/1998 | (WO) . |
| 98/53759 | 12/1998 | (WO) . |
| 98/57590 | 12/1998 | (WO) . |
| 98/57591 | 12/1998 | (WO) . |
| WO 98/57590 | 12/1998 | (WO) . |
| WO 98/57591 | 12/1998 | (WO) . |
| WO 98/57592 | 12/1998 | (WO) . |
| WO98/57592 * | 12/1998 | (WO) .................................. 606/194 |
| 99/08624 | 2/1999 | (WO) . |
| 99/49793 | 3/1999 | (WO) . |
| 99/15220 | 4/1999 | (WO) . |
| 99/17683 | 4/1999 | (WO) . |
| 99/21510 | 5/1999 | (WO) . |
| 99/22655 | 5/1999 | (WO) . |
| 99/22658 | 5/1999 | (WO) . |
| 99/25273 | 5/1999 | (WO) . |
| 99/36000 | 7/1999 | (WO) . |
| 99/36001 | 7/1999 | (WO) . |
| 99/38459 | 8/1999 | (WO) . |
| 99/40868 | 8/1999 | (WO) . |
| 99/48427 | 9/1999 | (WO) . |
| 99/48545 | 9/1999 | (WO) . |
| 99/49790 | 10/1999 | (WO) . |
| 99/49910 | 10/1999 | (WO) . |
| 99/51162 | 10/1999 | (WO) . |
| 99/52481 | 10/1999 | (WO) . |
| 99/53863 | 10/1999 | (WO) . |
| 00/57590 | 11/1999 | (WO) . |
| 99/55406 | 11/1999 | (WO) . |
| 99/60941 | 12/1999 | (WO) . |
| 99/62430 | 12/1999 | (WO) . |
| 00/09195 | 2/2000 | (WO) . |
| 00/12029 | 3/2000 | (WO) . |
| 00/15146 | 3/2000 | (WO) . |
| 00/15147 | 3/2000 | (WO) . |
| 00/15148 | 3/2000 | (WO) . |
| 00/15149 | 3/2000 | (WO) . |
| 00/15275 | 3/2000 | (WO) . |

| | | |
|---|---|---|
| 00/18302 | 4/2000 | (WO) . |
| 00/18325 | 4/2000 | (WO) . |
| 00/21436 | 4/2000 | (WO) . |
| 00/21461 | 4/2000 | (WO) . |
| 00/21463 | 4/2000 | (WO) . |

OTHER PUBLICATIONS

Richter, M.D. et al., "Transjugular Intrahepatic Portacaval Stent Shunt: Preliminary Clinical Results," *Radiology,* 1990, vol. 174, No. 3, pp. 1027–1030.

Zemel, M.D. et al., "Percutaneous Transjugular Portosystemic Shunt," *JAMA,* 1991, vol. 266, No. 3, pp. 390–393.

Massimo, M.D. et al., "Myocardial Revascularization by a New Method of Carrying Blood Directly from the left Ventricular Cavity into the Coronary Circulation," *Journal of Thoracic Surgeons,* Aug. 1997, vol. 34, No. 2, pp. 257–564.

Lary, M.D. et al., "Myocardial Revascularization Experiments Using the Epicardium," *Archives of Surgery,* Jan. 1969, vol. 98, No. 1, pp. 69–72.

Munro, M.D. et al., "The possibility of myocardial revascularization by creation of a left ventriculocoronary artery fistula," *Journal of Thoracic and Cardiovascular Surgery,* Jul. 1969, vol. 58, No. 1, pp. 25–32.

Kuzela, M.D. et al., "Experimental evaluation fo direct transventricular revascularization," *The Journal of Thoracic and Cardiovascular Surgery,* Jun. 1969, vol. 57, No. 6, pp. 770–773.

U.S. Ser. No. 09/315,383, filed May 18, 1999, pending.
U.S. Ser. No. 09/318,373, filed May 25, 1999, pending.
U.S. Ser. No. 09/368,393, filed Aug. 4, 1999, pending.
U.S. Ser. No. 09/368,483, filed Aug. 4, 1999, pending.
U.S. Ser. No. 09/368,644, filed Aug. 4, 1999, pending.
U.S. Ser. No. 09/368,868, filed Aug. 4, 1999, pending.
U.S. Ser. No. 09/369,048, filed Aug. 4, 1999, pending.
U.S. Ser. No. 09/369,061, filed Aug. 4, 1999, pending.
U.S. Ser. No. 09/534,038, filed Mar. 24, 2000, pending.
U.S. Ser. No. 60/147,202, filed Aug. 4, 1999, pending.
U.S. Ser. No. 60/147,209, filed Aug. 4, 1999, pending.
U.S. Ser. No. 60/147,210, filed Aug. 4, 1999, pending.
U.S. Ser. No. 60/147,211, filed Aug. 4, 1999, pending.
U.S. Ser. No. 60/147,218, filed Aug. 4, 1999, pending.
U.S. Ser. no. 60/153,205, filed Sep. 10, 1999, pending.
U.S. Ser. No. 09/534,038, filied Mar. 24, 2000, pending.
U.S. Ser. No. 60/201,732, filed May 4, 2000, pending.

\* cited by examiner

STENT DELIVERY SYSTEM AND METHOD OF USE

BACKGROUND OF THE INVENTION

1. Field of the Invention

The present invention relates to the delivery of a stent and other devices into the myocardium of a patient, and more particularly, to a stent delivery system to provide a bypass through the myocardium from the left ventricle into a coronary artery.

2. Description of the Related Art

Coronary arteries as well as other vessels frequently become clogged with plaque that at the very least impairs the efficiency of the heart's pumping action and can lead to heart attack and death. One conventional treatment for clogged coronary or other arteries is a bypass operation wherein one or more venous segments are inserted between the aorta and the coronary artery. The inserted venous segments or transplants act as a bypass of the clogged portion of the coronary artery and thus provide for a free or unobstructed flow of blood to the heart.

Such coronary artery bypass surgery, however, is expensive, time-consuming and traumatic to the patient. Hospital stays subsequent to the surgery and convalescence are prolonged.

A new coronary artery bypass technique is disclosed in U.S. Pat. No. 5,429,144. That technique utilizes a stent made of a biocompatible material and comprises steps of moving the stent in a collapsed configuration through a blood vessel of a patient's vascular system to the patient's heart, inserting the stent in the patient's myocardium, and upon disposition of the stent in the myocardium, expanding the stent from the collapsed configuration to a substantially tubular expanded configuration so that a blood flow path is formed at least partially through the myocardium.

One problem with the coronary artery bypass method providing a stent through the myocardium of the heart is how to get the stent into the myocardium. U.S. Pat. No. 5,429,144 describes a percutaneous approach wherein the stent is brought to the myocardium through the patient's vasculature on the distal end of a catheter, and advanced into the myocardium over a guidewire. One particular challenge is how to make an angled bend in the guidewire to puncture through the wall of the vessel and into the myocardium.

Another problem with this approach is that catheters delivering the guidewire, stent or other devices to be provided into the myocardium are conventionally guided to the puncture point through the blockage in the coronary artery. However, when the blockage is too large, a delivery catheter cannot access the desired insertion site.

In addition, it is often difficult to advance devices into the myocardium because of the traction and force necessary to push through the myocardium. This problem arises not only for delivery of the stent, but also for the delivery of dilation catheters used to expand the cross-section of the passageway through the myocardium, and other devices.

Accordingly, what is needed is a method and apparatus for delivering guidewires, stents and other devices into the myocardium. In particular, what is needed is a delivery system that can deliver these devices at an angled bend for transverse insertion into the myocardium. Moreover, what is needed is a delivery method and apparatus for advancing a delivery catheter to a puncture site in a coronary vessel when the blockage in the vessel is too large to permit passage of a catheter therethrough. What is also needed is a method and apparatus for advancement of a stent, dilation catheter or other device into and through the myocardium.

SUMMARY OF THE INVENTION

Briefly stated, the present invention addresses the above needs by providing various methods and apparatuses for delivering stents and other devices into the myocardium of a patient. One preferred stent delivery system provides access to the insertion site in the myocardium by advancing a delivery catheter through a blockage in a coronary artery, or around the blockage through a coronary vein or through a channel or tunnel formed around the blockage. In one embodiment, once the distal end of the delivery catheter is adjacent the myocardium, an angled bend is created in the catheter by actuating expandable steering guides mounted to the catheter which cooperate with the walls of the blood vessel to cause the catheter to turn. Then, a guidewire is advanced through the delivery catheter and into the myocardium. In another embodiment, a tip-deflecting pull wire extends from the distal end of the delivery catheter which may be actuated to turn towards and then inserted into the myocardium. In another embodiment, an exit port facing the insertion site is provided within the catheter or a balloon mounted on the catheter so that a guidewire may be directed through a lumen and out the exit port into the myocardium. Once the guidewire punctures into the myocardium, the guidewire is anchored using barbs, balloons or other actuatable members to secure the guidewire to the myocardium. Subsequently, using a push-pull mechanism, stents and other medical devices can be advanced over the guidewire into the myocardium.

In one aspect of the present invention, a guidewire is delivered into the patient such that the proximal end of the guidewire extends out of the patient, while the distal end of the guidewire is positioned adjacent the myocardium. The distal end of the guidewire is inserted into the myocardium, and the guidewire is then anchored to the myocardium. An introducer catheter carrying a medical device is advanced over the guidewire to deliver the device into the myocardium.

In another aspect of the present invention, a method for delivering a stent into the myocardium to bypass a blockage formed in a coronary artery is provided. A channel is created from a position proximal to the blockage in the coronary artery to a position distal to the blockage in the coronary artery. A guidewire is advanced through the channel until a distal end of the guidewire is adjacent the myocardium. The guidewire is inserted into the myocardium, and a stent is advanced over the guidewire into the myocardium.

In another aspect of the present invention, a method is provided for creating a bypass through the myocardium of a patient to bypass a blockage formed in a coronary artery. A first tunnel is created through the myocardium having a proximal end and a distal end. The proximal end of the tunnel opens into the coronary artery proximal to the blockage. The distal end of the tunnel is positioned within the myocardium. A second tunnel is created through the myocardium, the second tunnel having a first branch extending from the distal end of the first tunnel and opening into the coronary artery at a position distal to the blockage. A second branch of the second tunnel extends from the distal end of the first channel and opens into the left ventricle. A stent is disposed in the second tunnel to provide a myocardial passageway therethrough.

In another aspect of the present invention, a delivery catheter is provided. This delivery catheter comprises an elongate tubular body having a proximal end and a distal end and a lumen extending therethrough. A first steering member is mounted on the distal end of the tubular body, and a second steering member is mounted on the distal end of the tubular body at a position distal to that of the anchoring member.

In another aspect of the present invention, a method for turning a distal end of a catheter within a body lumen is provided. The catheter comprises an elongate tubular body having a proximal end and a distal end. An anchoring member mounted to the distal end is actuated to secure the catheter against the body lumen. A steering member is mounted to the distal end of the of the guidewire at a position distal to that of the anchoring member. When actuated, the steering member cooperates with the body lumen to turn the distal end of the catheter.

In another aspect of the present invention, a method is provided for delivering a medical device to a delivery site within a patient. This method comprises providing a delivery catheter having a proximal end and a distal end and a lumen extending therethrough into a body lumen of the patient. The delivery catheter is secured within the body lumen. The distal end of the catheter is turned by actuating a steering member mounted on the distal end of the catheter which pushes off against a wall of the body lumen. The medical device is advanced through the lumen of the delivery catheter and out the distal end.

In another aspect of the present invention, a method for delivering a stent into the myocardium of a patient is provided. A delivery catheter is advanced into the vasculature of the patient, the delivery catheter having a proximal end and a distal end and a lumen extending therethrough, until the distal end is adjacent the myocardium. A pull wire extending from the distal end of the delivery catheter is actuated to turn the pull wire toward the myocardium. The pull wire is advanced from the distal end of the delivery catheter into the myocardium. The stent is delivered over the pull wire into the myocardium.

In another aspect of the present invention, a method for delivering a stent into the myocardium of a patient is provided. A delivery catheter is advanced into the vasculature of the patient, the catheter having a proximal end and a distal end and a lumen extending from the proximal end to a side port near the distal end, until the side port faces the myocardium. A guidewire having a proximal end and a distal end is inserted into the lumen. The distal end of the guidewire is advanced through the lumen and out the side port. The guidewire punctures into the myocardium, and the stent is delivered over the guidewire into the myocardium.

In another aspect of the present invention, a method for delivering a stent into the myocardium of a patient is provided. A delivery catheter is advanced into the vasculature of a patient, the catheter having a proximal end and a distal end, until the distal end is adjacent the myocardium. An anchoring member mounted on the distal end of the catheter is expanded to secure the delivery catheter within the vasculature. A guidewire having a proximal end and a distal end is inserted through a lumen in the expanded anchoring member, the lumen extending from a proximal end of the anchoring member to a side port facing the myocardium, so that the distal end of the guidewire exits through the side port. The guidewire punctures into the myocardium, and the stent is advanced over the guidewire into the myocardium.

In another aspect of the present invention, a delivery catheter is provided. The catheter comprises an elongate body having a proximal end and a distal end. An expandable member is mounted on the distal end of the tubular body, the expandable member having a proximal end and a distal end and an exterior surface. A guide lumen extends from the proximal end of the balloon to a side port on the exterior surface of the expandable member for directing a medical device therethrough.

In another aspect of the present invention, a method for treating an aneurysm is provided. A catheter having a proximal end and a distal end is advanced to the site of the aneurysm. An expandable member mounted on the distal end of the catheter is actuated to substantially enclose the aneurysm. An embolic element is inserted through a lumen in the expandable member into the aneurysm.

In another aspect of the present invention, a method for delivering a medical device into a body tissue of a patient is provided. The method comprises inserting a guidewire having a proximal end and a distal end into the myocardium from a coronary blood vessel. The guidewire is anchored to the body tissue, and the medical device is pushed over the guidewire into the body tissue. The proximal end of the guidewire is correspondingly pulled proximally while the medical device is pushed distally in order to assist advancing the medical device through the body tissue.

In another aspect of the present invention, a delivery system for directing medical treatment at least partially into the myocardium is provided. The delivery system comprises a guidewire having a proximal end and a distal end, means for turning the distal end of the guidewire toward the myocardium, means for anchoring the guidewire to the myocardium, and a catheter carrying the medical treatment having a lumen extending therethrough for receiving the guidewire and advancing the catheter into the myocardium.

In another aspect of the present invention, a method for delivering a stent into the myocardium of a patient to bypass a blockage formed in a coronary artery is provided. The method comprises advancing a catheter having a proximal end and a distal end and a lumen extending at least partially therethrough from the proximal end to a distal opening through the coronary artery of the patient until the distal opening is past the blockage. The catheter is turned so that the distal opening faces the myocardium. A wire having a proximal end and a distal end is extended through the distal opening such that the distal end punctures into the myocardium. The distal end of the wire is anchored to the myocardium. A dilation catheter is delivered over the wire, the catheter carrying a dilation balloon on a distal end thereof, until the balloon is within the myocardium. The dilation balloon is inflated to create an opening in the myocardium. The dilation balloon is then deflated and the dilation catheter removed from the wire. A stent introducer catheter is delivered over the wire, the stent introducer catheter carrying a stent on a distal end thereof, until the stent is located within the opening in the myocardium. The stent is deployed within the opening in the myocardium.

In another aspect of the present invention, a method for delivering medical treatment into the myocardium of a patient is provided. A tubular wire is delivered into the patient, the wire having a lumen extending therethrough. The wire once delivered has a proximal end extending out of the patient and a distal end positioned adjacent the myocardium. Means for turning the distal end of the wire towards the myocardium are provided. Then, the distal end of the wire is inserted into the myocardium. Medical treatment is delivered through the lumen in the wire into the myocardium.

DETAILED DESCRIPTION OF THE PREFERRED EMBODIMENTS

The preferred embodiments described hereinbelow depict methods and apparatuses for delivering a stent into the myocardium to create a passageway between the left ventricle and coronary artery. It should be appreciated, however, that these embodiments may also be applied to the delivery of stents and other medical devices into other body tissues and vessels, and are particularly applicable for delivering devices at an angled bend relative to the axis of blood flow. In addition, the delivery methods and apparatuses described herein pertain to the placement of stents and other devices partially through the myocardium, as well as for drug delivery and similar applications.

Figure 1A:
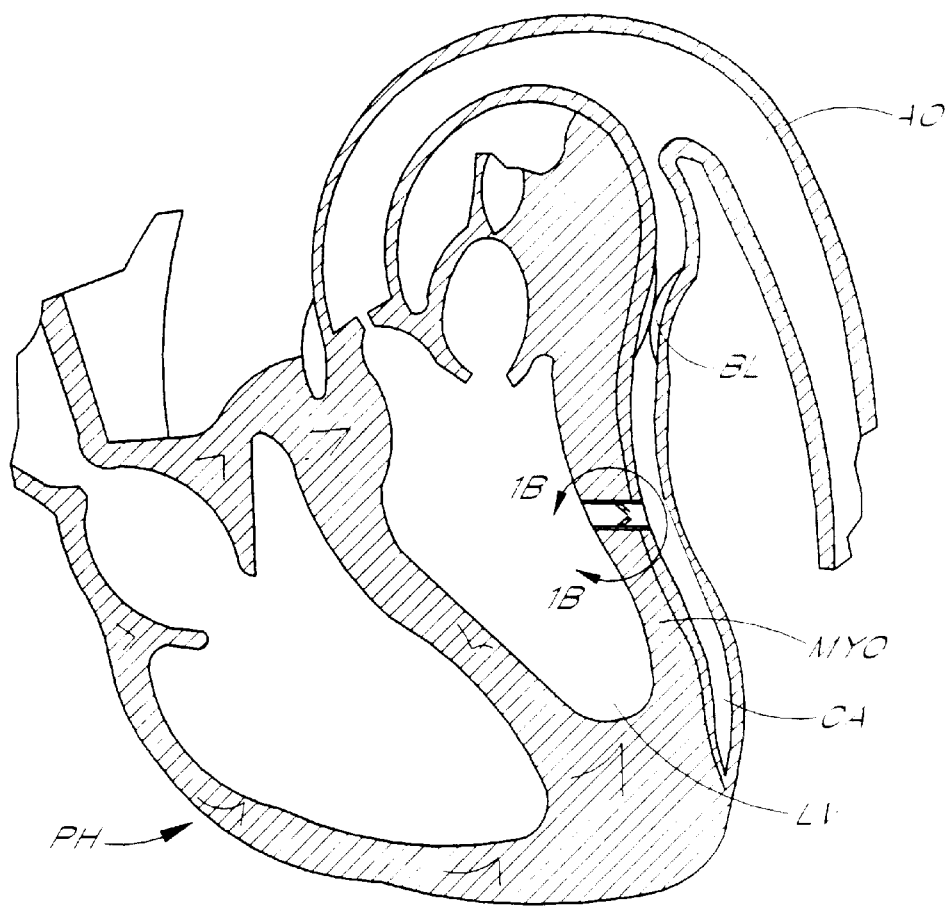
FIG. 1A is a schematic, cross-sectional view of a human heart, showing a stent in the myocardium of the heart for forming a bypass shunt between the left ventricle and a coronary artery.
Figure 1B:
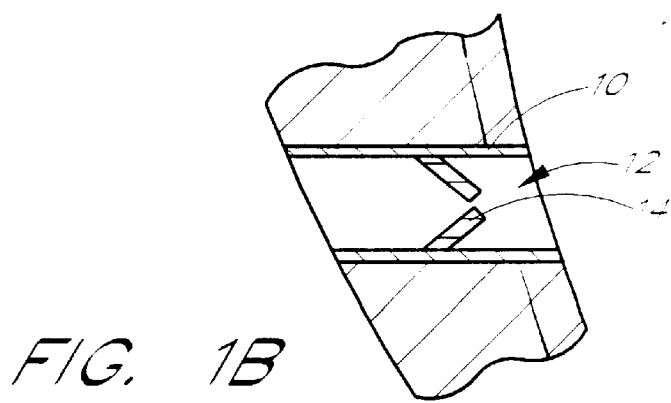
FIG. 1B is an enlarged view of the bypass shunt of FIG. 1A.

As illustrated in FIGS. 1A and 1B, a coronary artery bypass is accomplished by disposing a stent 10 in a heart wall or myocardium MYO of a patient's heart PH. Stent 10 preferably extends from the left ventricle LV of heart PH to a clogged coronary artery CA at a point downstream of a blockage BL to create a shunt 12 therethrough. Stent 10 is preferably made of a biocompatible material such as stainless steel or nitinol, although other materials such as Ti, Ti alloys, Ni alloys, Co alloys and biocompatible polymers may also be used. Stent 10 preferably has a one way valve 14 to allow blood to flow from the left ventricle LV to the coronary artery CA. Although the stent 10 may elastically deform under the contractive pressure of the heart muscle during systole, the stent remains open to allow blood to pass from the patient's left ventricle LV into the coronary artery CA. During diastole, the blood pumped into coronary artery through shunt 12 is blocked by one-way valve 14 from returning to left ventricle LV. Further details are disclosed in U.S. Pat. No. 5,429,144, the entirety of which is hereby incorporated by reference. Other types of stents may also be used in accordance with the preferred embodiments described herein.

Figure 2:
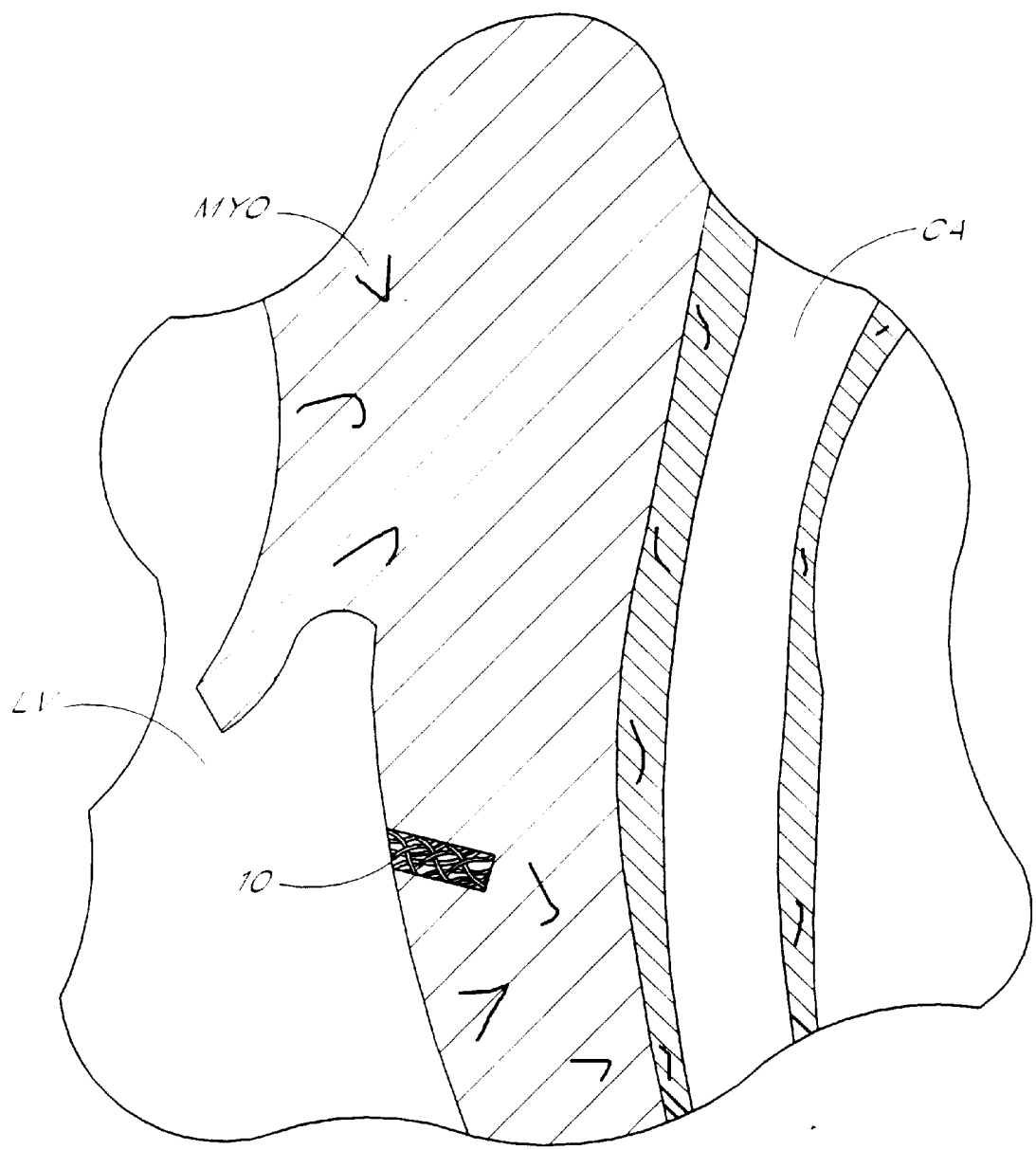
FIG. 2 is a schematic, partial cross-sectional view of a human heart, showing a stent extending partially into the myocardium from the left ventricle.

FIG. 2 illustrates another application for which it is desirable to dispose a stent into the myocardium of a patient. In this application, a stent 10 is provided partially through the myocardium MYO from the left ventricle LV. The stent 10 guides blood directly into the myocardium MYO from the left ventricle to replenish oxygen-deprived heart muscle. Further details are disclosed in the above-referenced U.S. Pat. No. 5,429,144. Other applications providing a stent in the myocardium, extending either partially or entirely therethrough and accessed from either the coronary artery or the left ventricle, are also contemplated by the present invention.

To achieve some or all of the objects of the present invention, in particular creating a myocardial passageway between the left ventricle LV and the coronary artery CA for disposition of a stent therein, requires a delivery system capable of directing the necessary devices to and into the myocardium. As described in further detail below, the suitable delivery system: (1) provides access to the insertion site adjacent the myocardium; (2) creates an angled bend for transverse insertion of devices into the myocardium; and (3) directs devices into the myocardium for creation of the myocardial passageway.

I. Access To The Myocardium

The delivery system described herein preferably comprises one or more catheters or guidewires inserted percutaneously into the body, such as through the femoral artery and advanced in the patient's vasculature through the aorta AO, shown in FIG. 1A. It should be appreciated that the percutaneous approach is not essential to achieve many of the objects of the invention, and therefore, an open-chest or other approach may also be used.

Figure 3A:
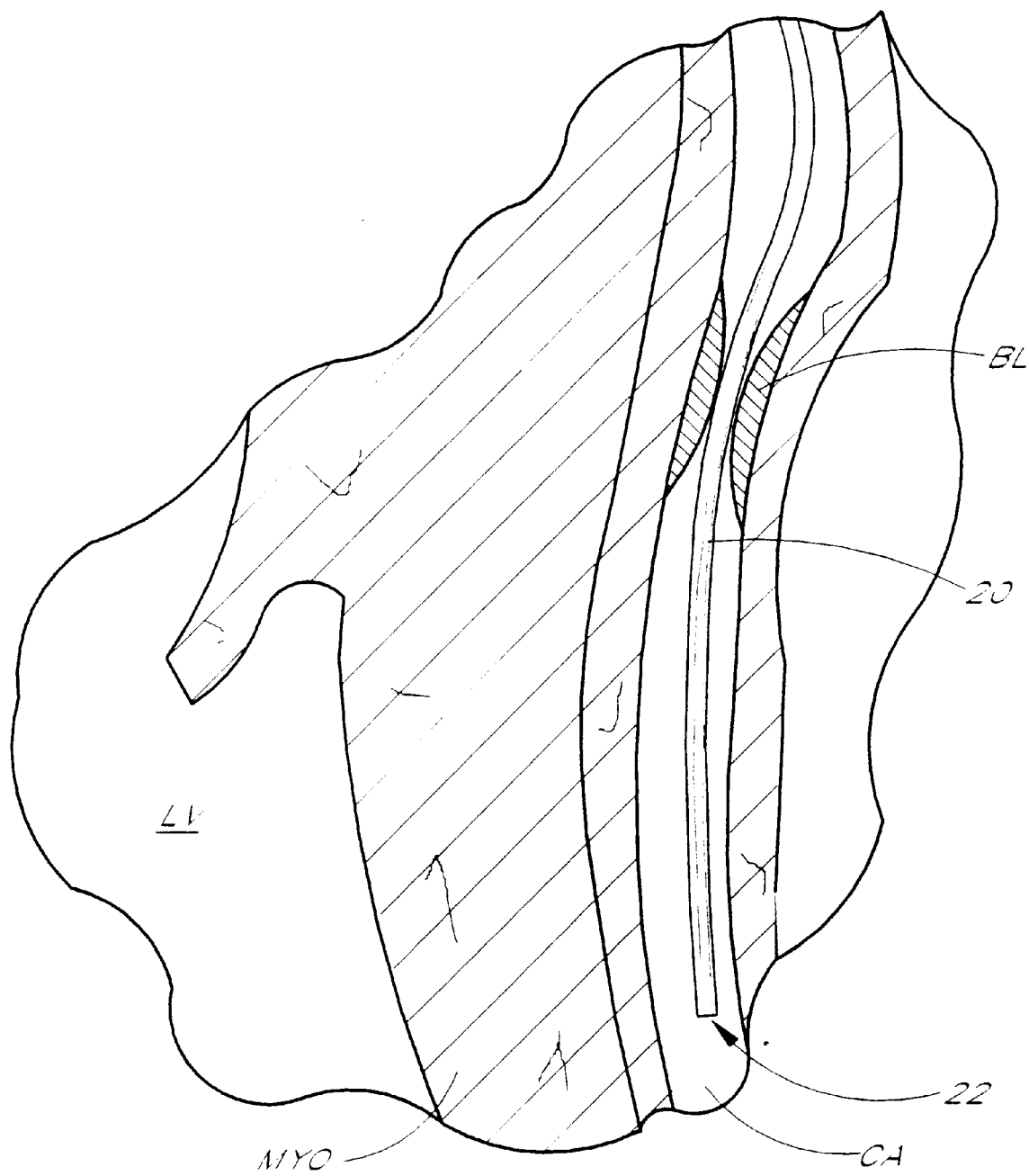
FIG. 3A is a schematic, partial cross-sectional view of a coronary artery adjacent the left ventricle, showing a delivery catheter being advanced through a blockage in the coronary artery.
Figure 3B:
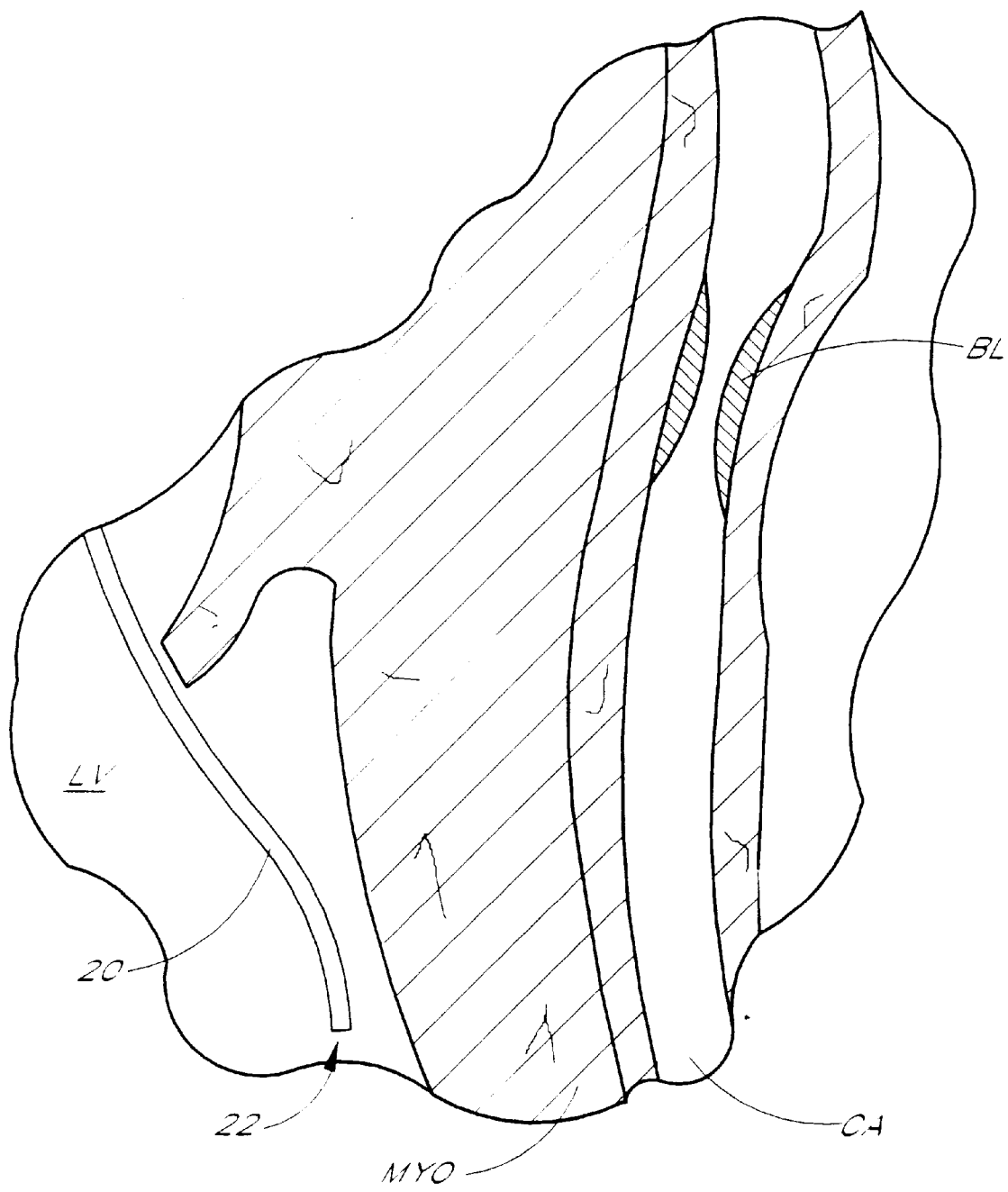
FIG. 3B is a schematic, partial cross-sectional view of a coronary artery adjacent the left ventricle, showing a delivery catheter being advanced into the left ventricle.

As shown in FIG. 3A, an exemplary delivery catheter or guidewire 20 which has been advanced percutaneously through the femoral artery and through aorta AO is advanced through the blockage BL in the coronary artery CA. The distal tip 22 of the catheter is delivered past the blockage so that it is positioned adjacent to a desired insertion point into the myocardium MYO. FIG. 3B shows an alternative access method wherein the catheter 20 is delivered to a position adjacent the myocardium through the left ventricle LV.

Figure 4A:
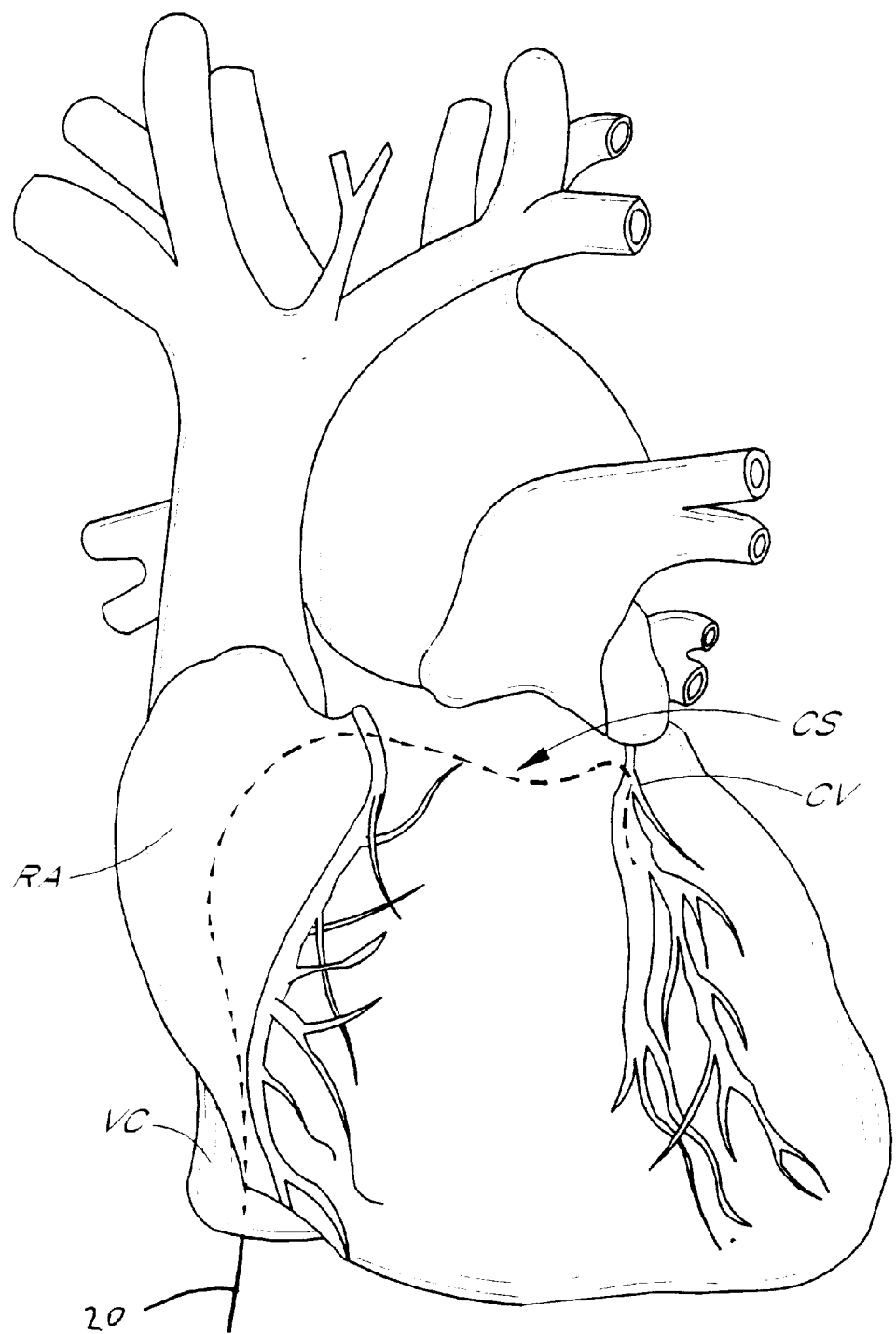
FIG. 4A is a schematic side view of a venous access route through a patient's heart.
Figure 4B:
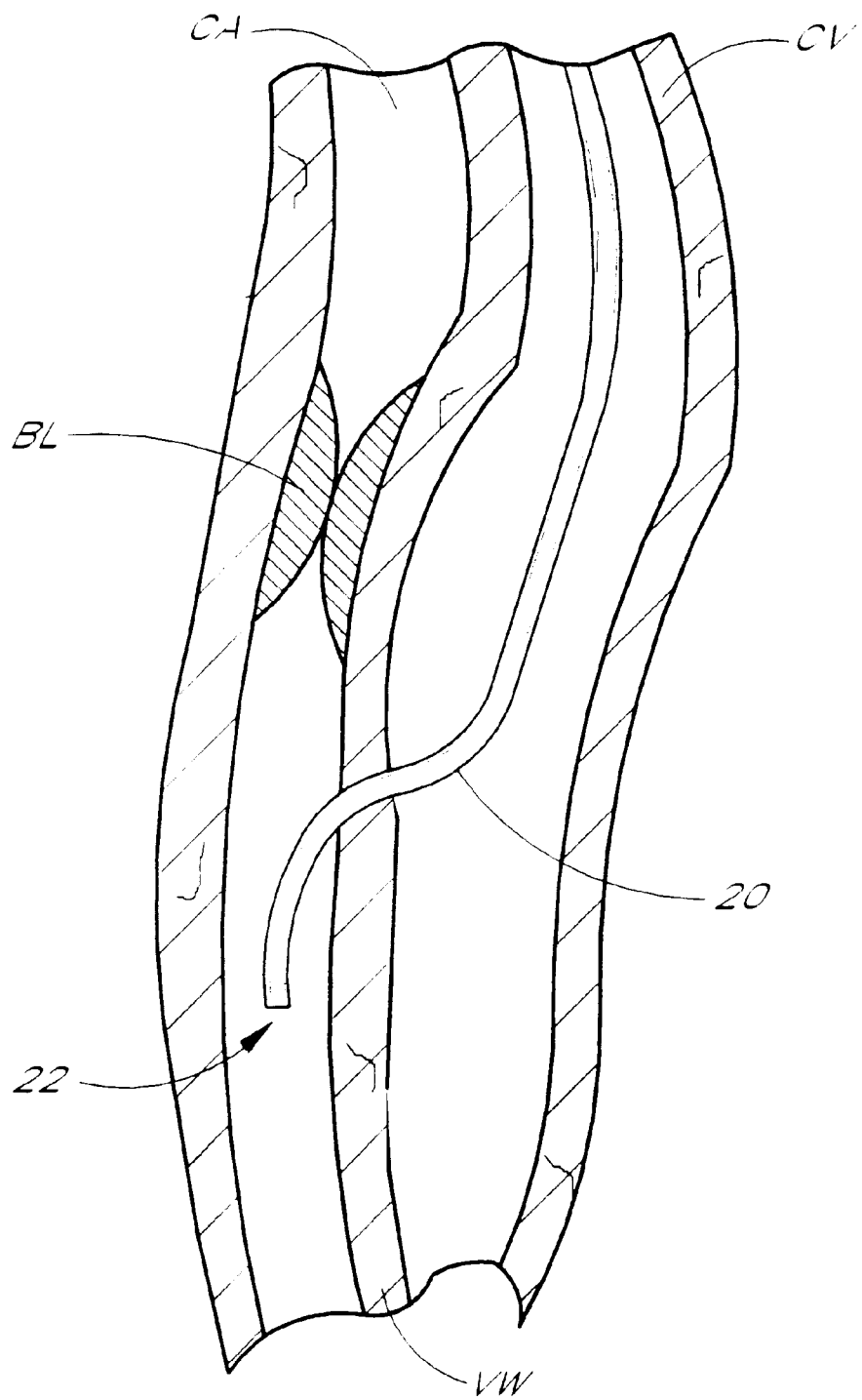
FIG. 4B is a schematic, partial cross-sectional view of the venous access route of FIG. 4A between a coronary vein and a coronary artery, showing a delivery catheter being advanced through the coronary vein into the coronary artery.

FIGS. 4A and 4B depict an alternative access route used when a blockage in the coronary artery is too large for the catheter to be passed therethrough. In this alternate embodiment, a delivery catheter 20 enters the body through an access point preferably in the femoral vein (not shown). The catheter is advanced up the vein to the vena cava VC and into the right atrium RA, as shown in FIG. 4A. Then, the catheter 20 is directed into the coronary sinus CS, and then to the coronary vein CV which runs adjacent to the coronary artery CA.

As shown in FIG. 4B, after the distal tip 22 of catheter 20 is past the blockage BL in the adjacent coronary vein, the delivery catheter 20 is inserted through the vessel wall VW separating the coronary vein CV from the coronary artery CA. Steering of catheter 20 between coronary vein CV and coronary artery CA may be accomplished using the methods and apparatus for turning catheters discussed in further detail below, or other suitable methods. As described in further detail below, the delivery catheter is turned toward the myocardium MYO either for insertion into the myocardium or for directing a guidewire to puncture therethrough. Access to the insertion point may also be accomplished by steering the delivery catheter through the coronary artery CA to a point proximal to the blockage, directing the catheter into the coronary vein to bypass the blockage, and reinserting the catheter from the coronary vein into the coronary artery past the blockage, as shown in FIG. 4B.

Figure 5:
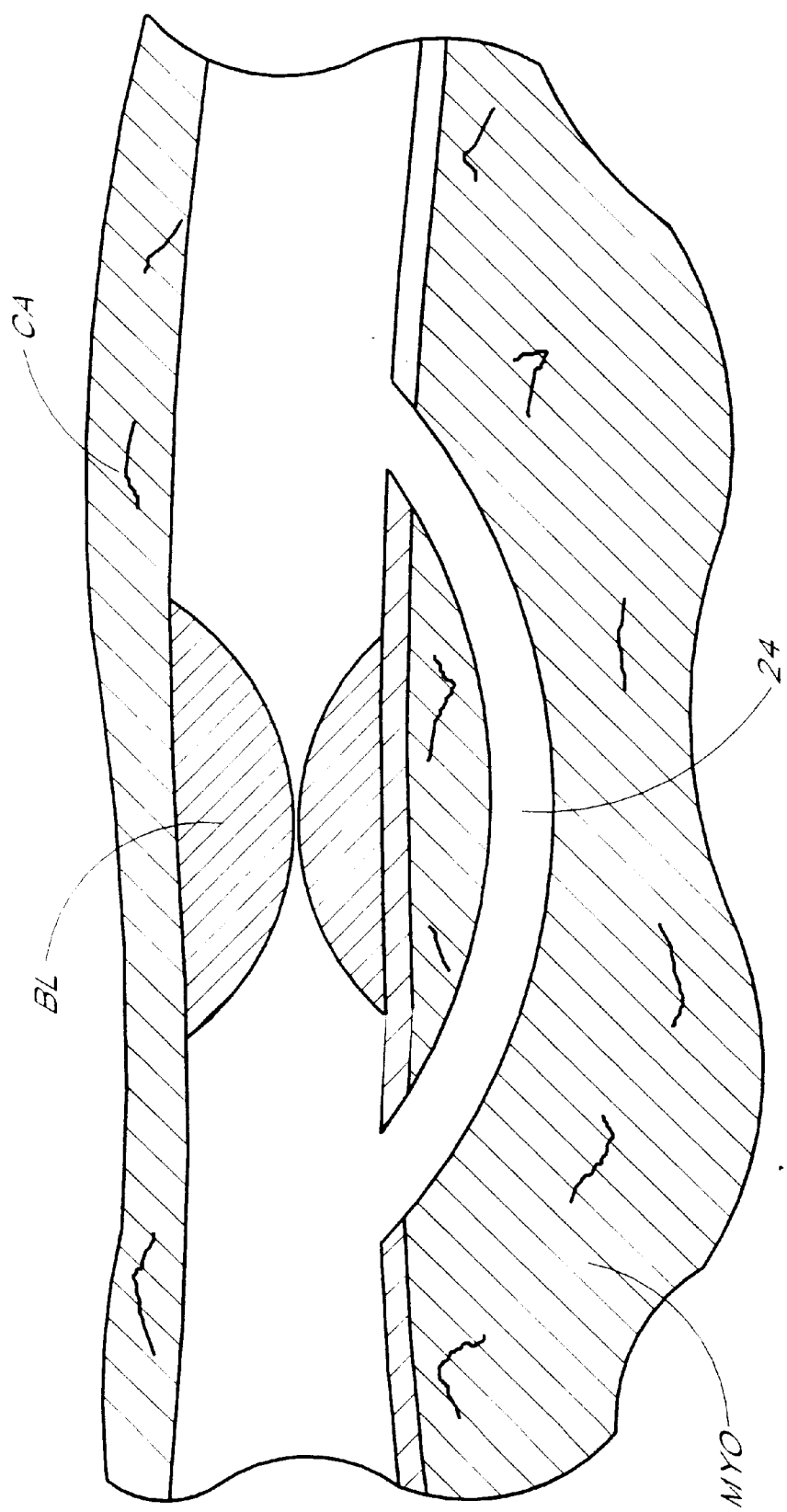
FIG. 5 is a schematic, partial cross-sectional view of a coronary artery adjacent the left ventricle, showing a tunnel formed through the myocardium to bypass a blockage in the coronary artery.
Figure 6:
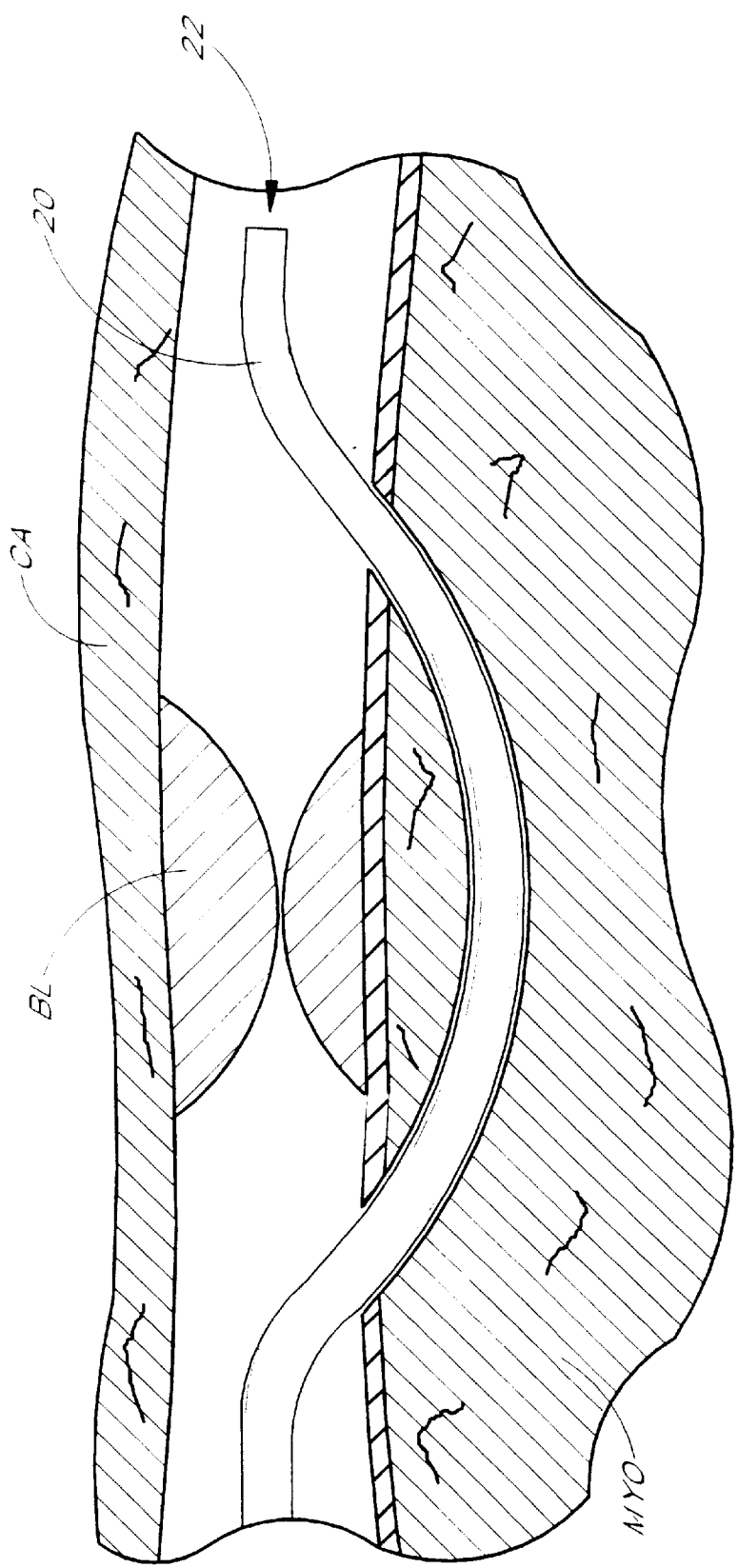
FIG. 6 is a schematic, partial cross-sectional view of a coronary artery adjacent the left ventricle, showing a delivery catheter being advanced through a tunnel formed through the myocardium.

An alternative method of accessing the myocardium MYO when the blockage BL is too large to pass a catheter therethrough employs creating a channel around the blockage. As illustrated in FIG. 5, a tunnel 24 is created from the coronary artery CA into the myocardium MYO at a point proximal to the blockage BL. The tunnel may be created using radiation, lasers, or a surgical drill, or any other suitable methods for creating a tunnel. The tunnel 24 extends underneath the blockage BL and connects with the coronary artery CA at a point distal to the blockage BL. As shown in FIG. 6, a delivery catheter 20 is advanced through the coronary artery CA, into the tunnel 24, and back into the coronary artery CA past the blockage BL. It will be appreciated that other methods for diverting a delivery catheter around a blockage may be used, such as directing the catheter through a shunt into the pericardial space outside the coronary artery.

While the tunnel 24 shown in FIG. 6 is described as providing access to a myocardial insertion point for a coronary bypass, it should also be appreciated that this tunneling technique may be useful for obliteration of the blockage BL. In particular, conventional methods for ablating a blockage only permit access to the blockage from one side. By employing the tunneling method shown in FIG. 6, however, a blockage BL can be treated not only from its proximal end, but also from its distal end simultaneously.

Figure 7:
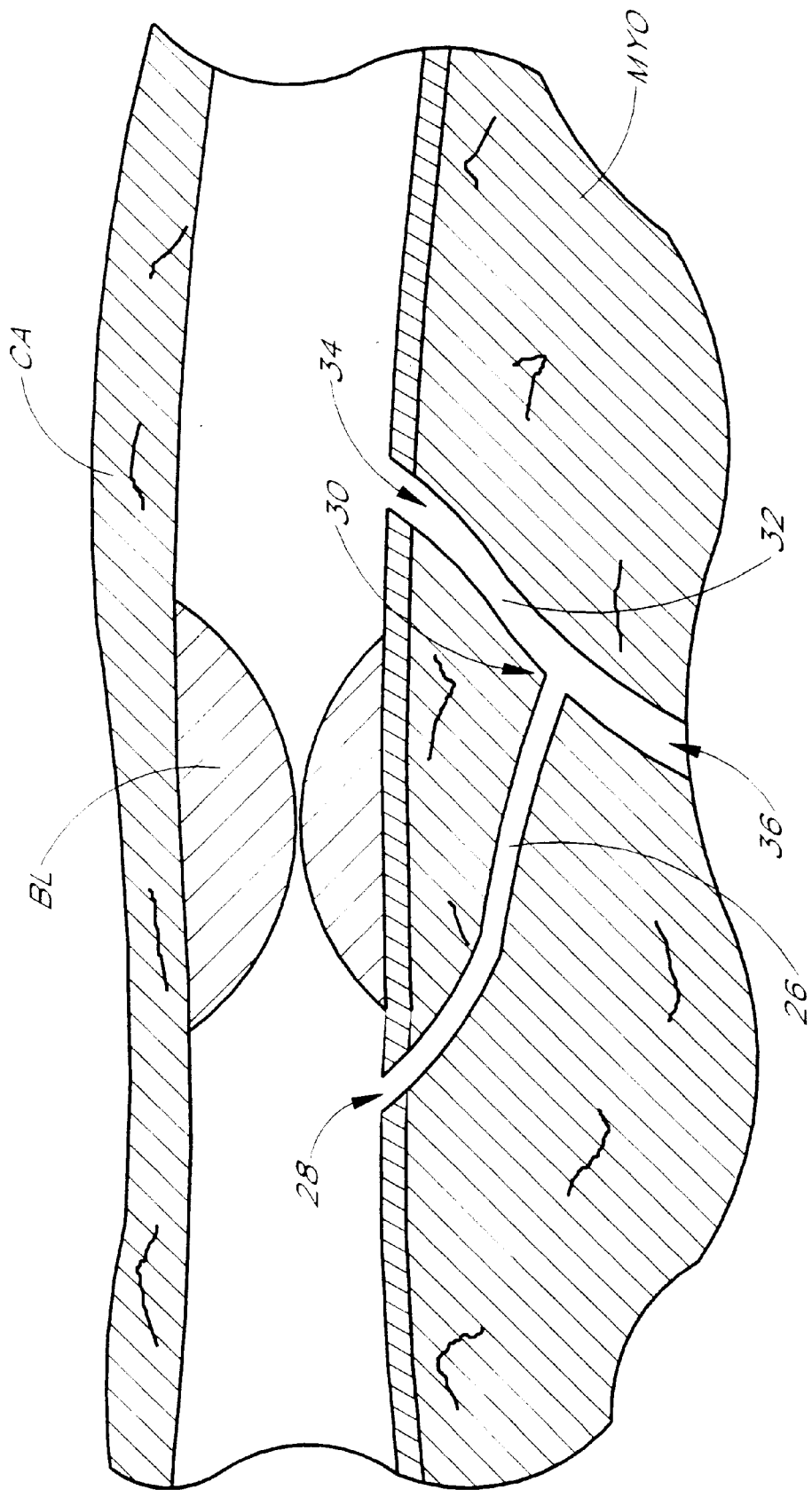
FIG. 7 is a schematic, partial cross-sectional view of a coronary artery adjacent the left ventricle, showing a Y-shaped tunnel formed through the myocardium to bypass a blockage in the coronary artery.

In an alternative embodiment, a tunnel is created through the myocardium MYO from a point proximal to a blockage in the coronary artery into the left ventricle. As shown in FIG. 7, where a blockage BL substantially occludes a coronary artery CA, a first tunnel 26 is formed proximally of the blockage BL extending into the myocardium MYO beneath the blockage BL. The tunnel 26 has a proximal end 28 which opens into the coronary artery CA proximal to the blockage BL, and a distal end 30 within the myocardium MYO beneath the blockage BL. A second tunnel 32 extends from the distal end 30 of the first tunnel, with a first branch 34 opening a channel to the coronary artery CA past the location of the blockage BL. A second branch 36 of the second tunnel 32 extends downward from the distal end 30 and opens into the left ventricle LV. As illustrated in FIG. 7, a substantially Y-shaped passageway is thereby created through the myocardium MYO to bypass the blockage BL.

Figure 8:
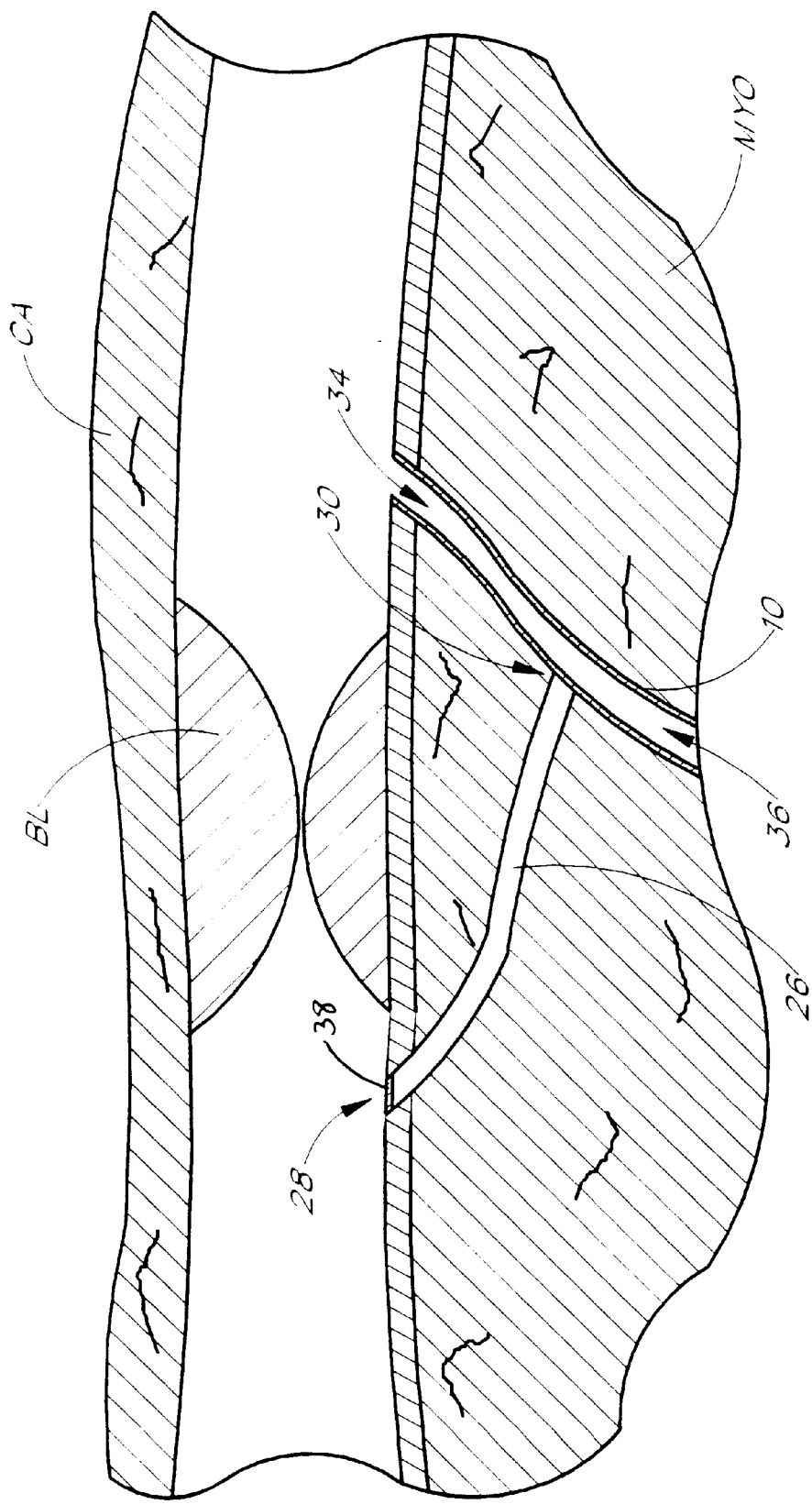
FIG. 8 is a partial cross-sectional view of the Y-shaped tunnel of FIG. 7, showing a stent provided therein.

As shown in FIG. 8, after formation of the Y-shaped passageway in the myocardium MYO, one or more stents 10 are provided in the second tunnel 32 extending between the left ventricle LV and the coronary artery CA. This stent 10 opens the myocardial passageway which provides the bypass past blockage BL. Positioning of stent 10 in the tunnel 32 is preferably accomplished by advancing a guidewire through the first tunnel 26 and into each branch 34 and 36 of the second tunnel 32, and then advancing the stent over the guidewire in the manner described below. After placement of the stent, the tunnel 26 between the coronary artery CA and stent 14 is preferably closed at least at distal end 30, and more preferably, also at proximal end 28. Closure of the tunnel may be accomplished by inserting plugs or other blocking means 38, or by sealing the tunnel with sutures or similar methods. Other suitable closure means include occlusion coils and balloons, adhesives such as cyanoacrylate, and plugs such as sold under the trade name GELFOAM. Alternatively, the tunnel may be closed due to the natural contraction of the openings 28 and 30 over time.

II. The Delivery Catheter

Once access to the desired insertion site is achieved, an appropriate delivery system is brought to the site. The preferred embodiments described hereinbelow are directed to a delivery system for inserting stents and other medical devices into the myocardium at an angle relative to the axis of blood flow. It should be appreciated that the angle of insertion may be adjusted between 0 and 180 degrees depending on the desired application. Furthermore, while the delivery systems below describe insertion of devices into the myocardium, these systems also enable angled delivery of medical devices into and through other body lumens and tissues.

A. Dual Balloon Delivery System

Figure 9:
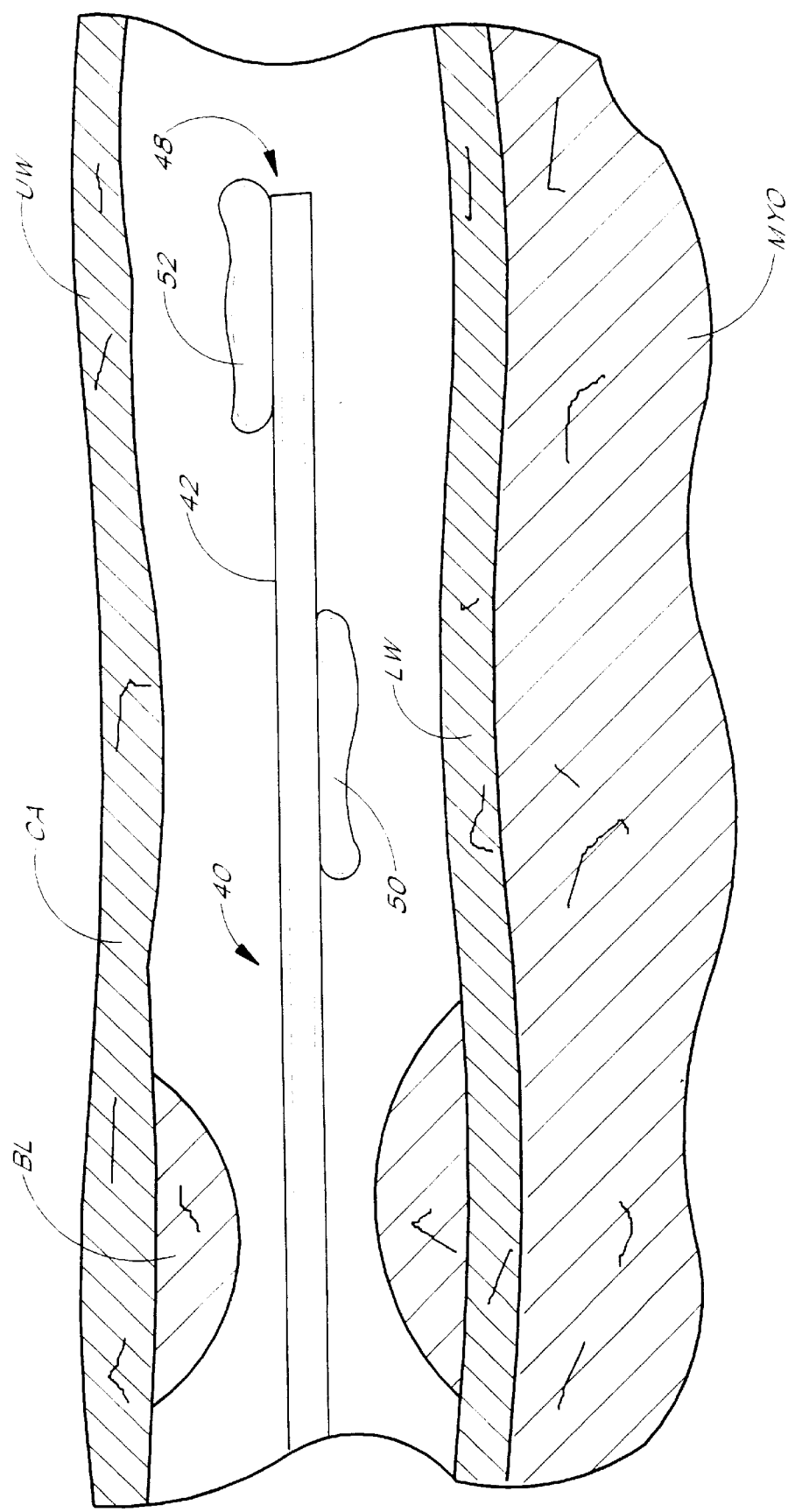
FIG. 9 is a side view of a delivery catheter carrying two uninflated steering balloons in a blocked coronary artery, with the artery shown partially cut away.

In one embodiment, the stent delivery system comprises a catheter which creates an angled bend for insertion of devices into the myocardium MYO. FIG. 9 illustrates a delivery catheter 40 which has been advanced into the coronary artery CA past the blockage BL. Catheter 40 is an elongate tubular body 42 having a lumen 44 (not shown) extending from a proximal end 46 (not shown) to a distal end 48. The catheter 40 is preferably formed from a flexible biocompatible material such as polymers, stainless steel or nitinol.

Mounted adjacent distal end 48 of catheter 40 are two steering guides, which are preferably expandable members such as inflatable balloon 50 and 52. As illustrated, a steering member, such as balloon 52, is preferably located distally of an anchoring member, such as balloon 50, such that steering balloon 52 is disposed near or at the very distal tip 48 of the catheter 40. Balloons 50 and 52 are each preferably mounted on opposite sides of the catheter tubular body 42, such that anchoring balloon 50 is mounted facing lower wall LW adjacent the myocardium MYO, and steering balloon 52 is mounted facing upper wall UW opposite lower wall LW. Alternatively, the anchoring balloon 50 may be mounted concentrically around the tubular body 42 so that inflation of the balloon expands against both the upper and lower walls. It will be appreciated that other devices, such as filters, posts and other expandable members may be used for the anchoring and/or steering members.

Figure 10:
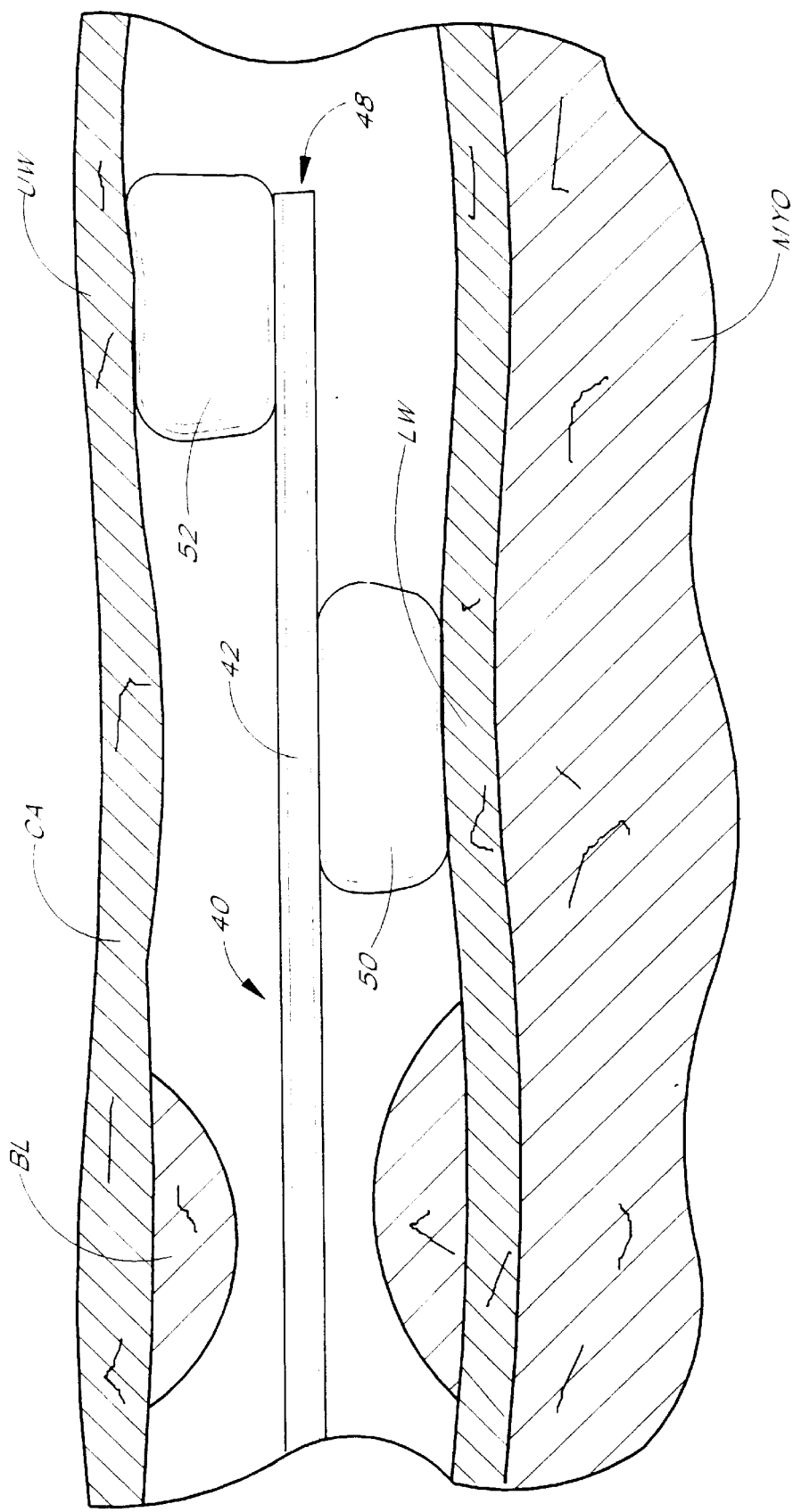
FIG. 10 is a side view of the delivery catheter of FIG. 9, showing the two balloons partially inflated.

As shown in FIG. 9, as the catheter 40 is advanced into position adjacent the myocardium MYO, the balloons 50 and 52 remain uninflated. As illustrated in FIG. 10, once the distal tip 48 of the catheter 40 is positioned adjacent the desired insertion site into the myocardium MYO, the balloons 50 and 52 are inflated. Inflation causes the balloons 50 and 52 to cooperate with the walls of the blood vessel to turn the distal end of the catheter. More particularly, in an intermediate state, anchoring balloon 50 inflates against the lower wall LW of the coronary artery CA, while steering balloon 40 presses against the upper wall UW.

Figure 11:
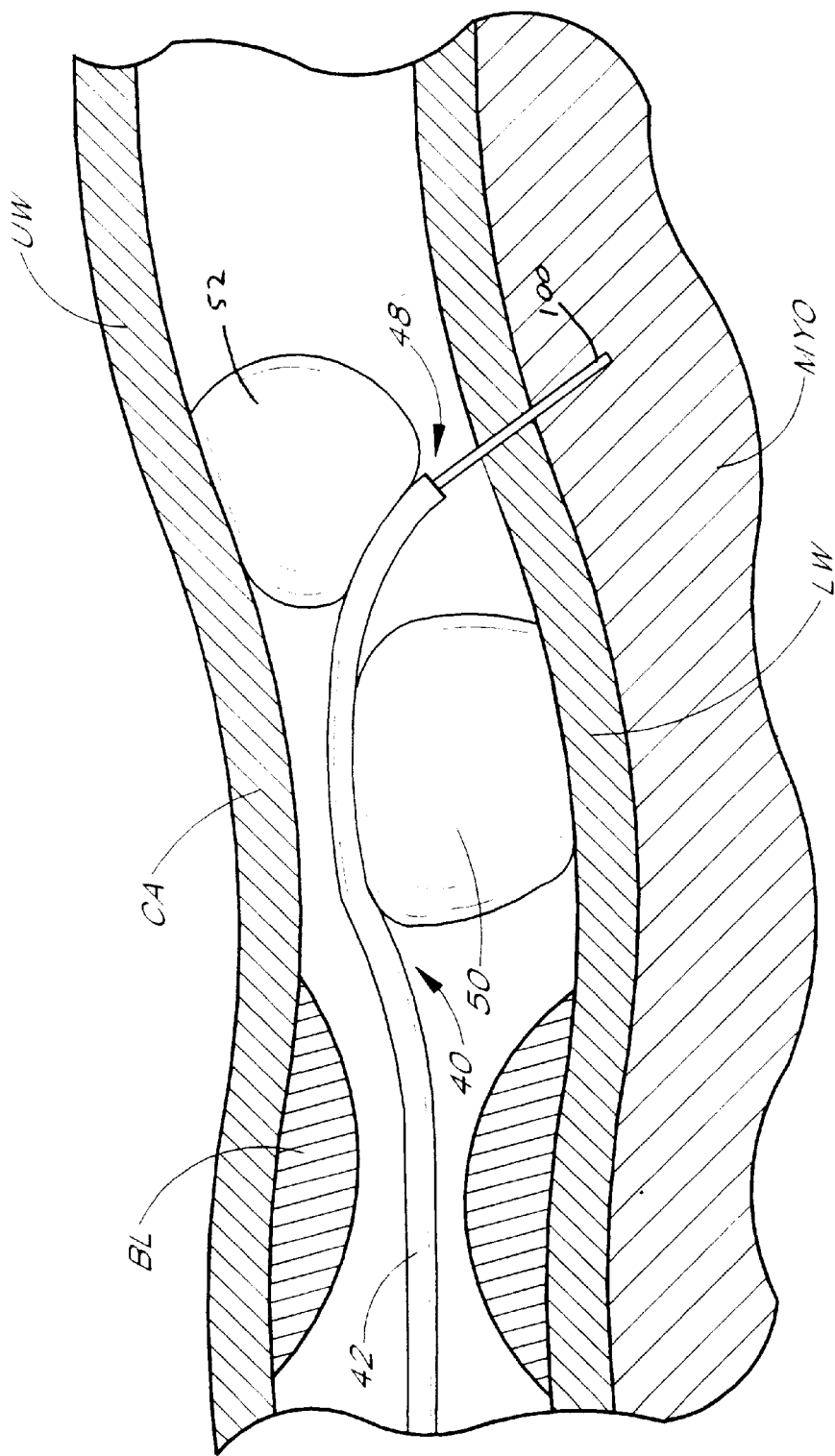
FIG. 11 is a side view of the delivery catheter of FIG. 9, showing the two balloons fully inflated and a guidewire extending from the distal end of the delivery catheter.

As illustrated in FIG. 11, anchoring balloon 50 acts to secure the tubular body 42 within the coronary artery CA. Inflation of balloon 50 also preferably causes the catheter 40 to displace in a direction opposite lower wall LW, thereby placing the catheter into a better position for transverse insertion of the distal end 48 into the myocardium MYO. Steering balloon 52 is further inflated, causing the distal tip 48 of the tubular body 32 to turn downward towards lower wall LW and myocardium MYO due to the resistance provided by upper wall UW against the balloon. FIG. 11 also illustrates the effect that the dual balloon inflation may have on the upper and lower walls of the coronary artery CA. When balloons 50 and 52 are fully inflated, forces created on the lower wall LW and upper wall UW, respectively, may cause the walls to shift at least slightly in the direction of balloon inflation. In particular, the lower wall LW may have a tendency to bend upwards distally of the balloon 50 toward the distal end 48 of delivery catheter 40 to assist in angling of the catheter.

Due to the turning action of catheter 40 caused by inflation of balloons 50 and 52, as well as the bending of lower wall LW toward distal end 48, once inflation of the balloons 50 and 52 is complete, the distal tip 48 of catheter 30 is positioned at a substantially transverse angle to the lower wall LW of the coronary artery CA and the myocardium MYO. From this position, the catheter 40 may serve as a guide for the delivery of devices used in creating a myocardial passageway. For example, as shown in FIG. 11 and described in further detail below, a puncture wire or guidewire 100 is advanced through the lumen 44 of tubular body 42, and then ejected out the distal tip 48 of the catheter 40 to puncture the lower wall LW into the myocardium MYO.

B. Pull Wire Actuator

Figure 12:
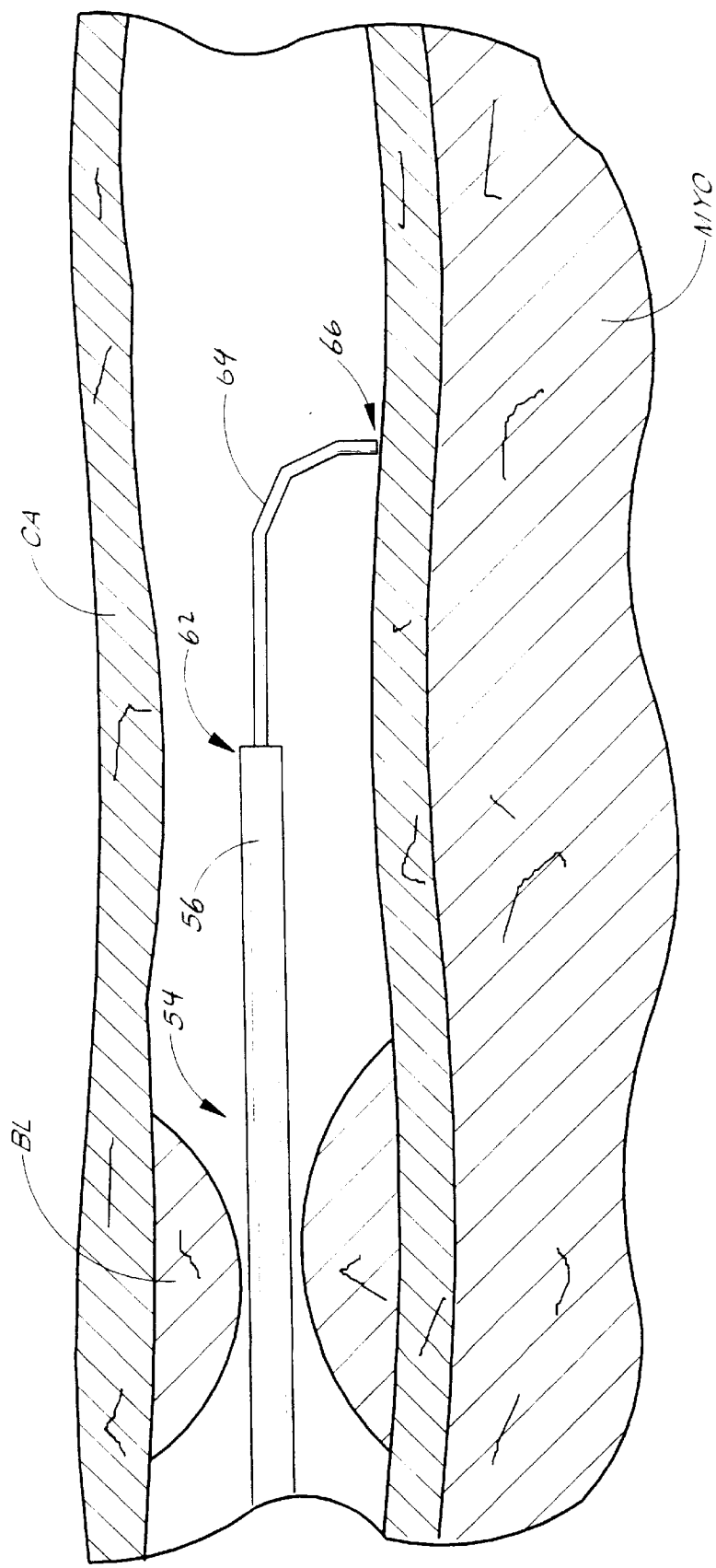
FIG. 12 is a side view of a delivery catheter with a tip deflecting wire in a blocked coronary artery, with the artery shown partially cut away.

FIG. 12 illustrates another embodiment for delivering devices transversely into the myocardium MYO of a patient's heart. A catheter 54 is shown extending through the coronary artery CA past a blockage BL. Catheter 54 comprises an elongate tubular body 56 with a lumen 58 (not shown) extending therethrough from a proximal end 60 (not shown) to a distal end 62. A tip-deflecting puncture wire or pull wire 64 extends from the distal end 62 of the catheter 54. The wire 64 is actuated at the proximal end (not shown) so that it deflects to form a near 90 degree angle relative to the catheter 54. The distal tip 66 of wire 64 is turned so that it is provided adjacent the myocardium MYO. This shape can be locked and the wire 64 is pushed forward through the coronary artery CA and into the wall of the myocardium MYO. As described in further detail below, with the wire 64 in place medical devices are delivered over the wire into the myocardium.

C. Side Port

Figure 13A:
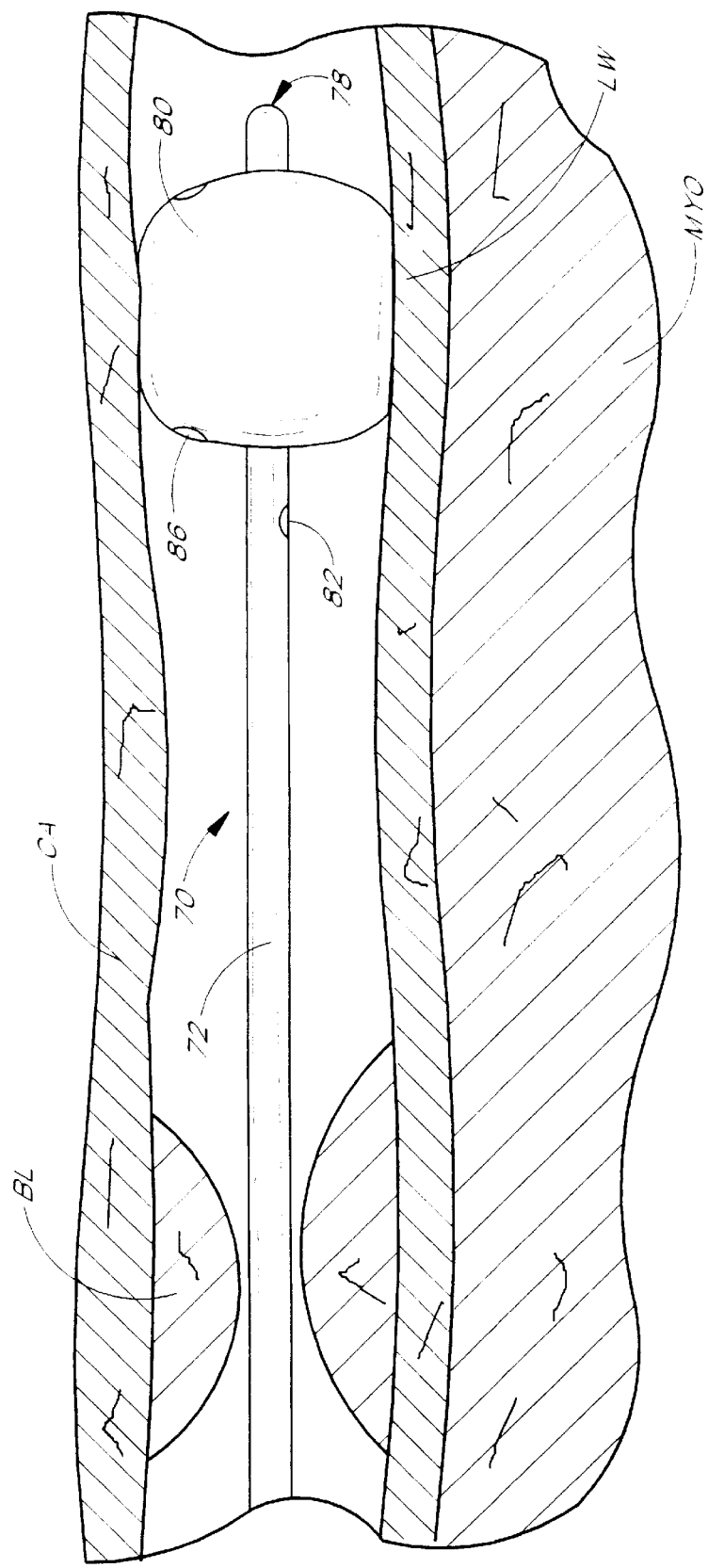
FIG. 13A is a side view of a delivery catheter having a side port proximal to an inflatable balloon in a blocked coronary artery, with the artery shown partially cut away.
Figure 14A:
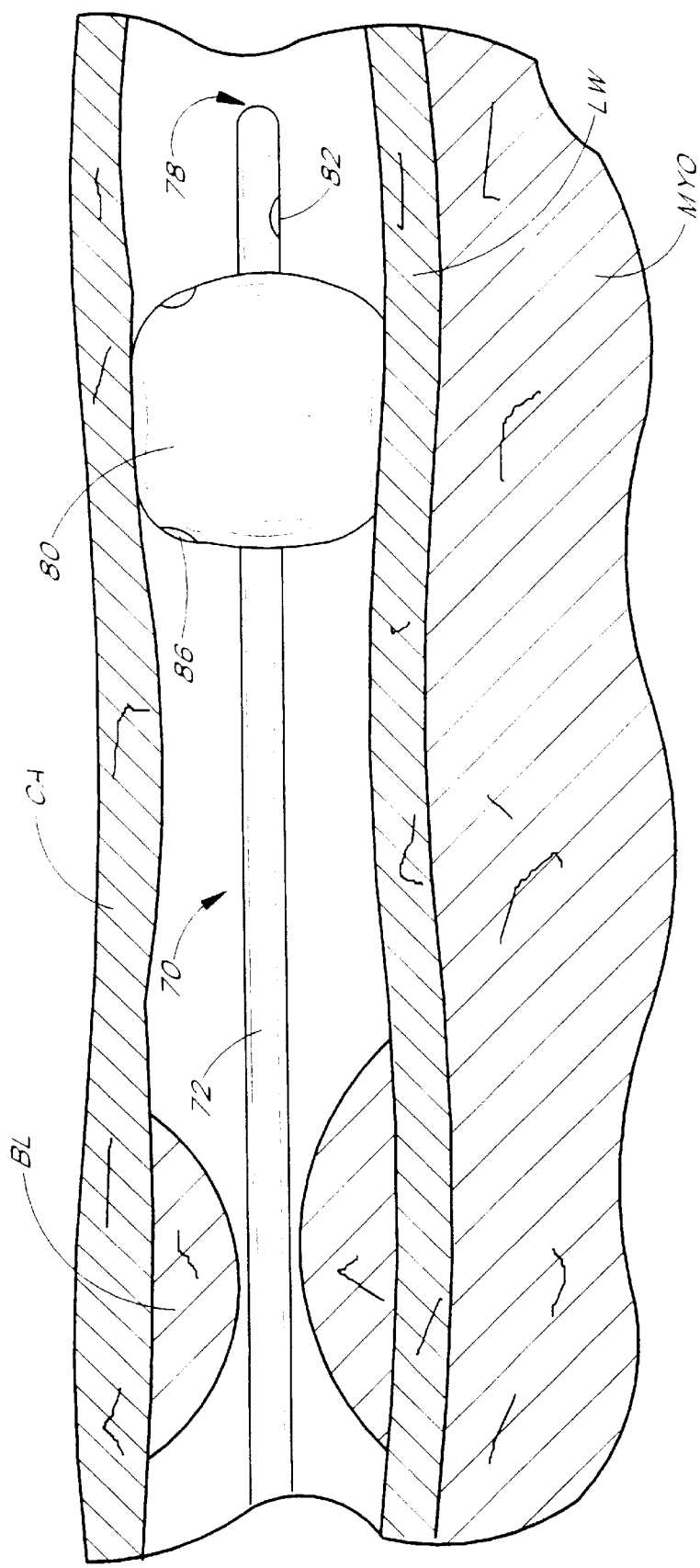
FIG. 14A is a side view of a delivery catheter having a side port distal to an inflatable balloon in a blocked coronary artery, with the artery shown partially cut away.

In another embodiment, a delivery catheter is provided with a side port which allows a puncture wire to exit therethrough. As shown in FIGS. 13A and 14A, delivery catheter 70 comprises an elongate tubular body 72 having a proximal end 76 (not shown) and a distal end 78 and a lumen 74 (not shown) extending at least partially therethrough. Preferably, mounted on distal end 78 is an expandable or anchoring member such as inflatable balloon 80, which is inflated to maintain the position of the catheter 70 within the artery. The balloon 80 is preferably a perfusion type balloon having a channel 86 to allow blood flow through the artery during the procedure. Alternatively, filters or other devices which allow blood flow through the artery while anchoring the catheter 70 may also be utilized. Perfusion may also be provided through a lumen in the tubular body 72. A distal opening or side port exit 82 is provided through the wall of tubular body 72 near the distal end of the catheter extending from lumen 74. The side port 82 may be located either proximal to the balloon 80, as in FIG. 13A, or distal to the balloon 80, as in FIG. 14A. Catheter 70 is delivered through the vasculature until the side port exit 82 is past the location of the blockage BL. Prior to balloon inflation, the catheter 70 is turned about its longitudinal axis so that the opening 82 faces the myocardium.

Figure 13B:
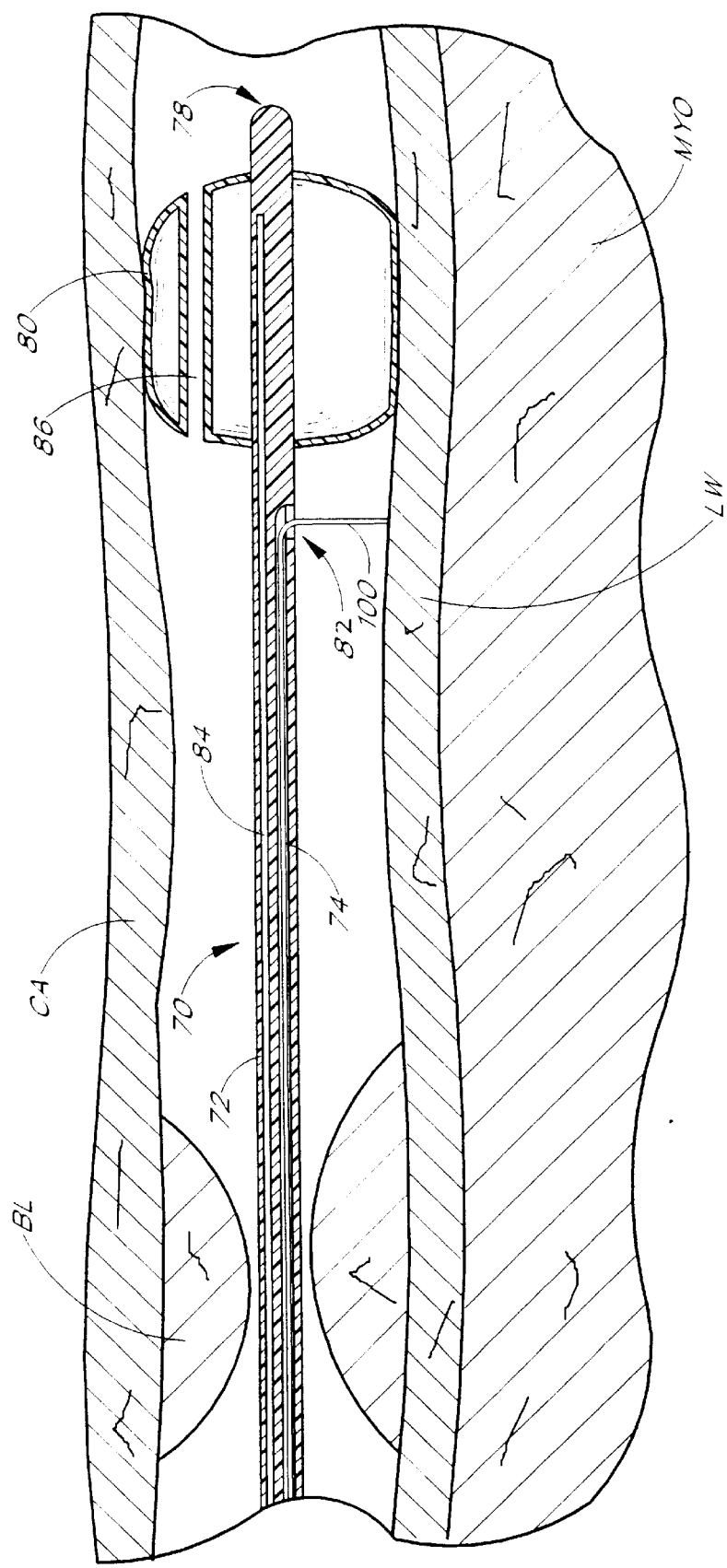
FIG. 13B is a cross-sectional view of the delivery catheter of FIG. 13A, further showing a guidewire extending therethrough.
Figure 14B:
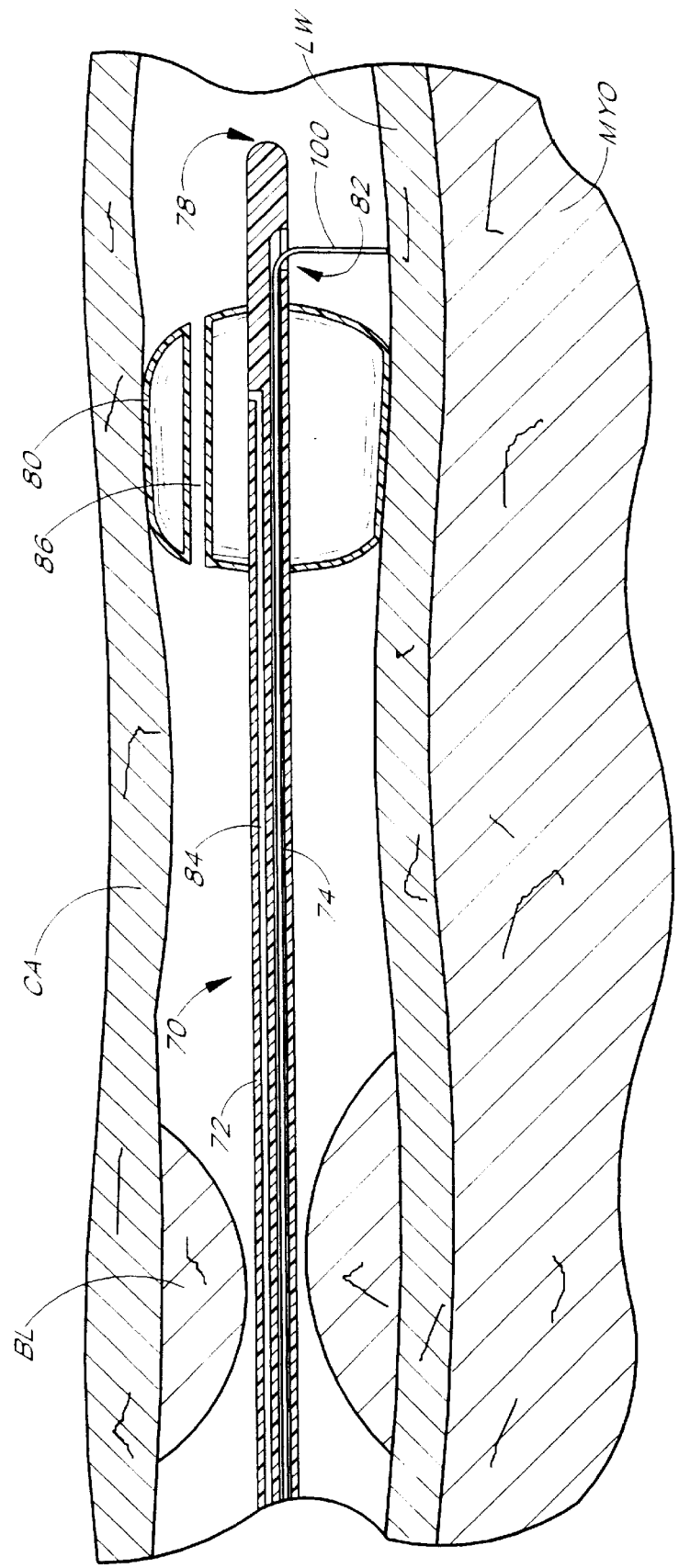
FIG. 14B is a cross-sectional view of the delivery catheter of FIG. 14A, further showing a guidewire extending therethrough.

FIGS. 13B and 14B illustrate the pathway for a guidewire 100 to pass through the lumen 74 of catheter 70. In FIG. 13B, guidewire 100 extends through the lumen 74 toward the distal end 78 of the catheter. Proximal to balloon 80, the lumen 74 turns downward toward side port exit 82. Thus, before guidewire 100 reaches the proximal end of balloon 80, the guidewire 100 is directed out of the side port 82 toward the lower wall LW of the coronary artery CA. A second lumen 84 is also provided within catheter 70 to direct inflation fluid to balloon 80.

FIG. 14B shows substantially the same configuration except that the lumen 74 extends through the balloon 80 such that the side port exit 82 is located distal to the balloon 80. Guidewire 100 therefore extends through lumen 74 and out side port exit 82 toward the lower wall LW. As with FIG. 13B, a second lumen 84 is provided through tubular body 72 to direct inflation fluid into the balloon 80.

Figure 15A:
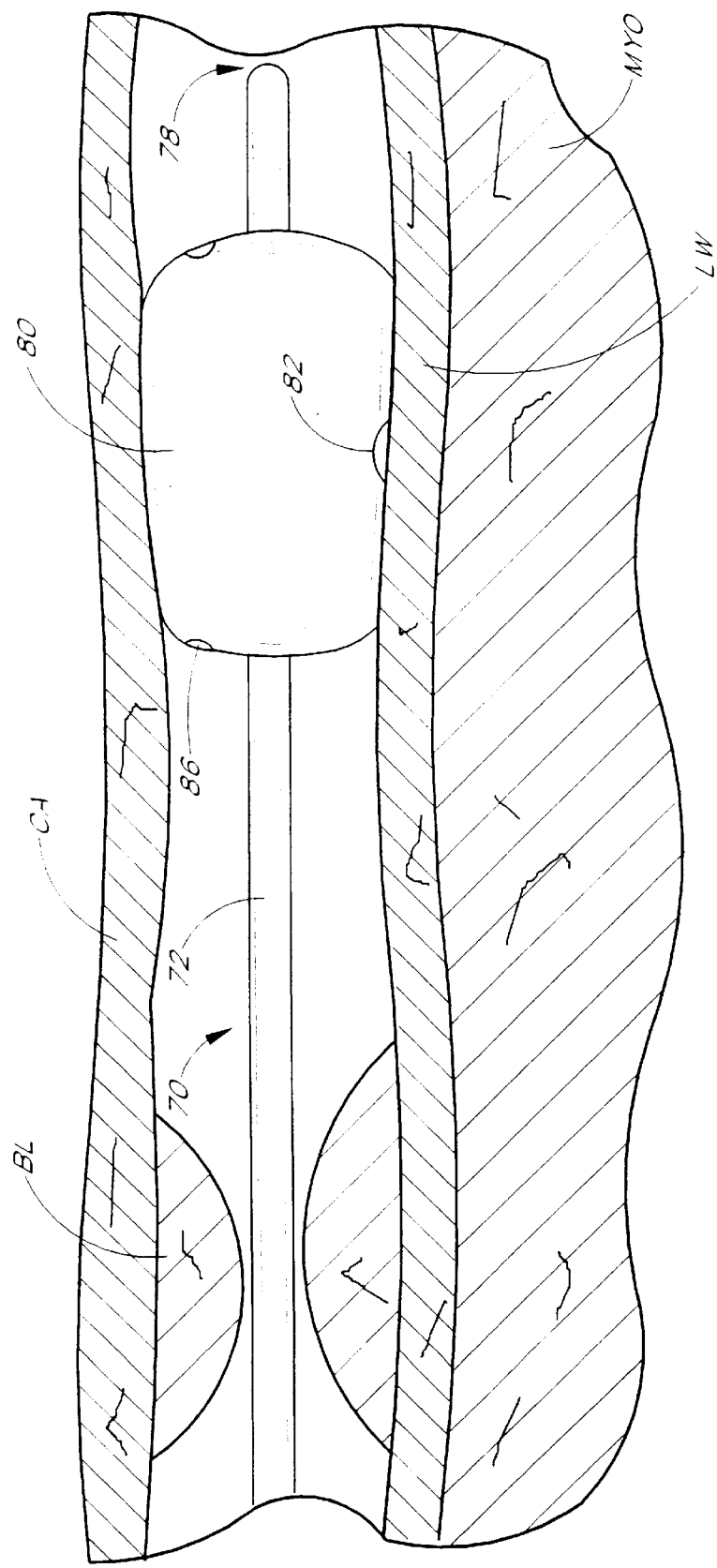
FIG. 15A is a side view of a delivery catheter having a side port within an inflatable balloon in a blocked coronary artery, with the artery shown partially cut away.
Figure 15B:
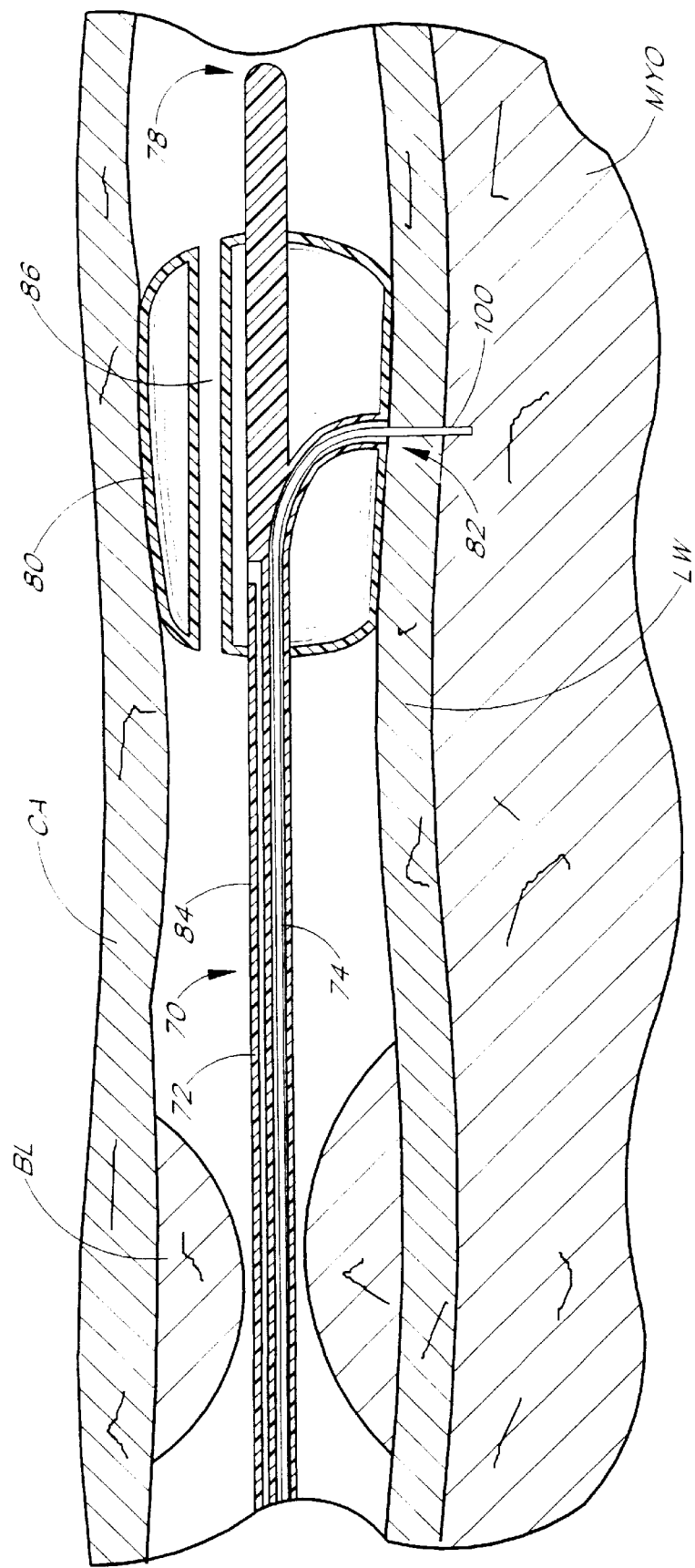
FIG. 15B is a cross-sectional view of the delivery catheter of FIG. 15A, further showing a guidewire extending through the balloon.

In another embodiment, as shown in FIG. 15A, the side port 82 is located on an exterior surface of the balloon 80. After the catheter 70 is delivered to a location past the blockage BL, balloon 80 is inflated. As shown in the cross-sectional view of FIG. 15B, balloon 80 preferably comprises a perfusion channel 86 extending from the proximal end to the distal end of the balloon 80 to allow blood to flow through the vessel. A lumen 74 is provided through the catheter 70 which extends into balloon 80 and turns downward into side port exit 82. The catheter 70 also has a lumen 84 for inflation of balloon 80. Guidewire 100 is advanced through lumen 74 and out side port exit 82 into the myocardium MYO.

Figure 15C:
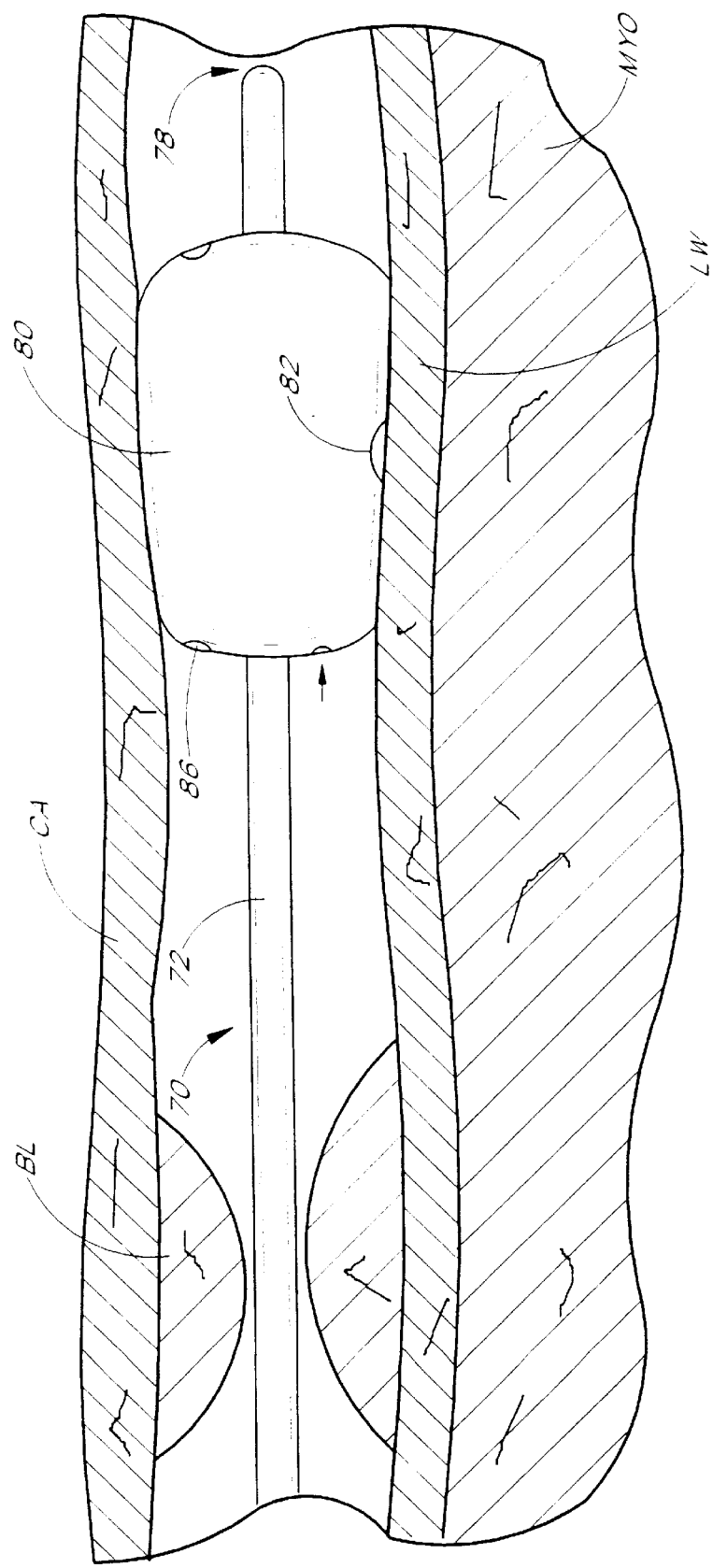
FIG. 15C is a side view of an alternative embodiment of a delivery catheter having a side port within an inflatable balloon in a blocked coronary artery, with the artery shown partially cut away.
Figure 15D:
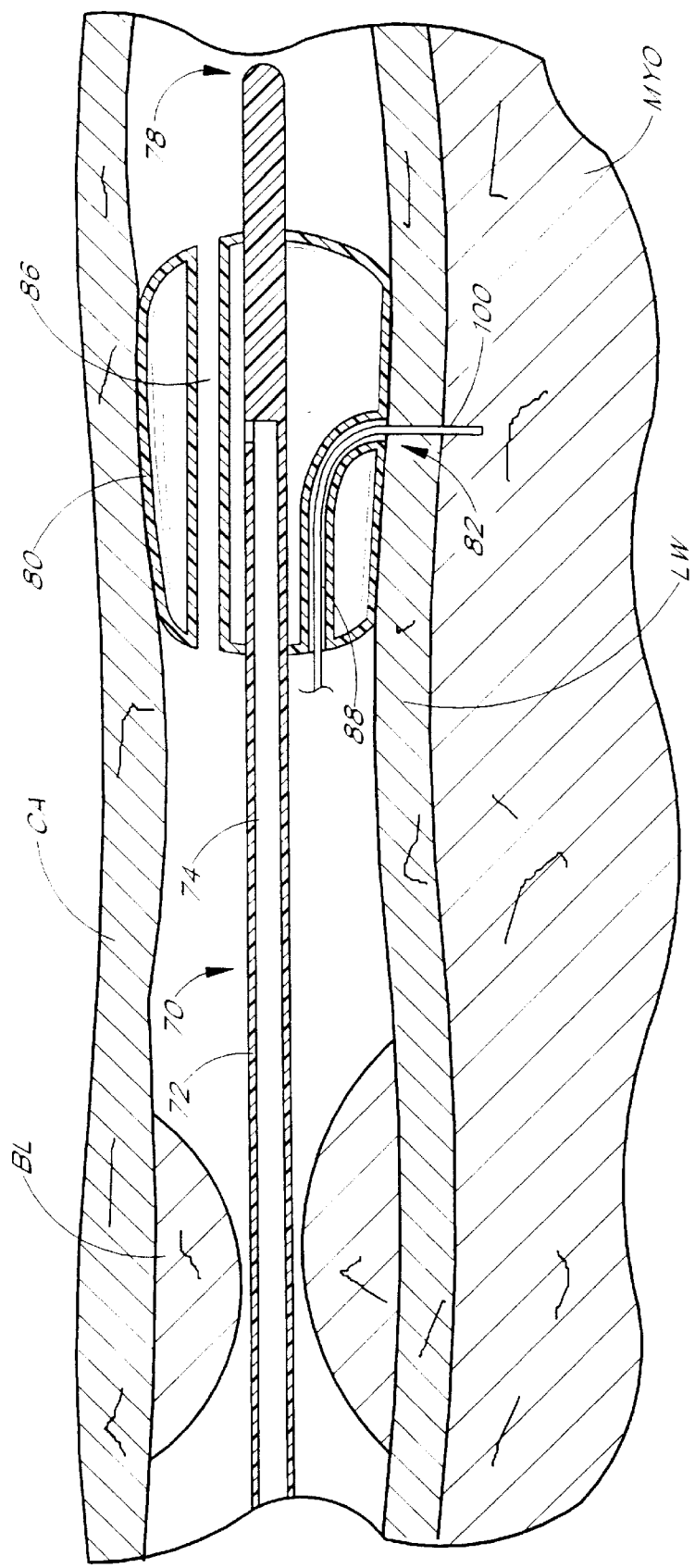
FIG. 15D is a cross-sectional view of the delivery catheter of FIG. 15C, further showing a guidewire extending through the balloon.

FIGS. 15C and 15D illustrate yet another embodiment of a delivery catheter with a side port exit. The catheter 70 comprises an elongate tubular body 72 having a lumen 74 extending from a proximal end 76 (not shown) to distal end 78. This lumen 74 is in fluid communication with balloon 80 to provide inflation of the balloon. When inflated, balloon 80 has a perfusion lumen 86 which allows blood to perfuse therethrough. The balloon 80 also has a guide lumen 88 extending therethrough which, when inflated, extends from a proximal end of the balloon to the lower wall LW. A guidewire 100 may then be inserted through the guide lumen 88 and out side port exit 82 into the myocardium MYO.

Figure 16:
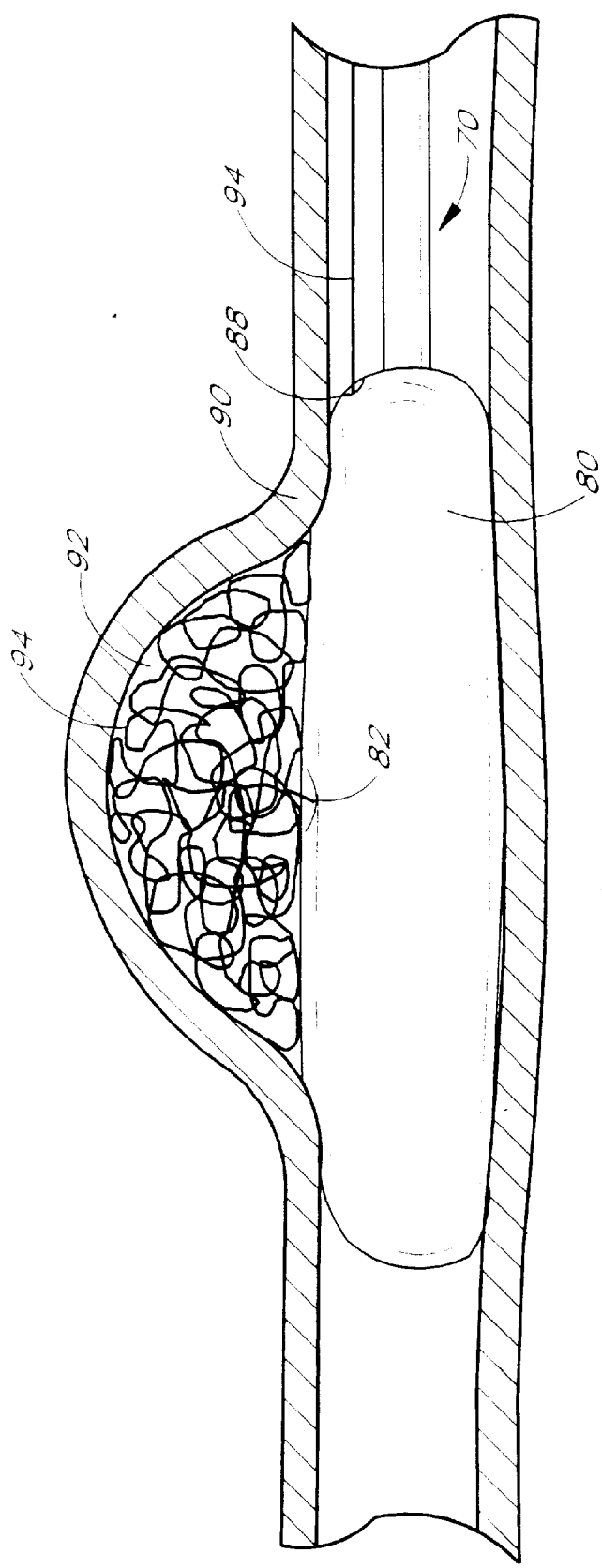
FIG. 16 is a side view of a delivery catheter having a side port within an inflatable balloon used for treating an aneurysm in a blood vessel, with the vessel shown partially cut away.

The delivery catheters described and shown in FIG. 15A–15D are useful not only for disposing a stent into the myocardium but also for the treatment of aneurysms. Aneurysms are typically treated by introducing embolic elements to fill the aneurysm. When the aneurysm opens substantially into the blood vessel, it becomes difficult to retain the embolic elements within the aneurysm while the aneurysm is being filled. FIG. 16 illustrates a method for solving this problem using the delivery catheter 70 described above with respect to FIGS. 15C and 15D. In a blood vessel 90 with an aneurysm 92, a catheter 70 carrying inflatable balloon 80 is advanced such that the balloon 80 is adjacent the aneurysm 92. The balloon 80 is inflated to substantially enclose the aneurysm 92. A wire 94 or other embolic element is advanced through the guide lumen 88 of balloon 80 and out side port 82. The wire 94 fills up the aneurysm 92, and is maintained in the aneurysm due to the fact that the balloon 80 encloses the aneurysm to prevent wire 94 from extending into the vessel. It should be appreciated that the wire 94 or other embolic element may also be delivered through a lumen 74, as shown with respect to the embodiment in FIG. 15B. After the aneurysm 92 is filled with wire 94, the wire 94 is cut, the balloon 80 is deflated, and the catheter 70 is removed from the vessel.

II. Anchoring Guidewire

The embodiments described above are directed primarily to providing a guidewire 100 into the patient's myocardium. As described in further detail below, this guidewire is used for delivering medical devices into the myocardium. However, it should be appreciated that many of the embodiments described above may also be used in conjunction with other methods for creating a passageway through the myocardium. For instance, a delivery catheter, such as described above, may be used for delivering a surgical drill or other tissue penetrating device ejected from the distal end thereof. This approach would be useful, for instance, in creating a tunnel through the myocardium as described above. Alternatively, a Seldinger wire may be ejected from the distal end of the delivery catheter. Further details are described in the above-referenced U.S. Pat. No. 5,429,144.

Figure 17:
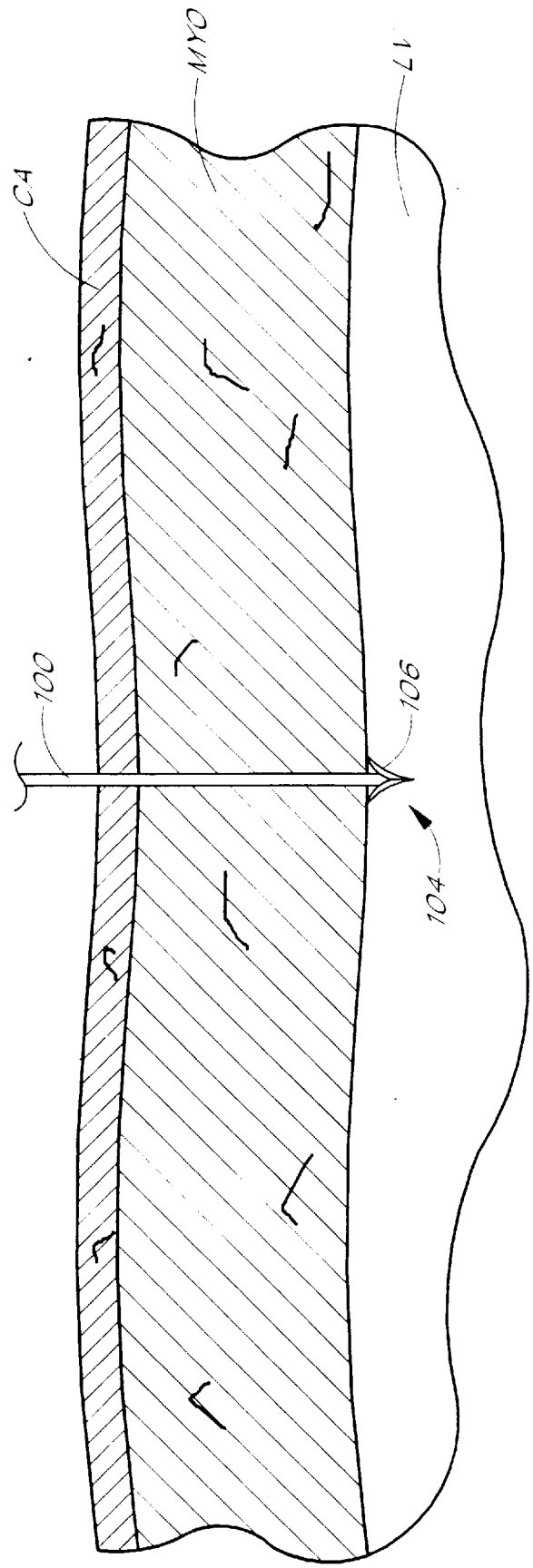
FIG. 17 is a side view of an anchoring guidewire extending through the myocardium, with the myocardium shown partially cut away.

As shown in FIG. 17, a puncture device such as guidewire 100 is directed into the myocardium 100 using any of the preferred methods described above. Guidewire 100 preferably has a proximal end 102 (not shown) which remains outside the patient's body, and a distal end 104 which is inserted through a delivery catheter as described above. Where the delivery catheter is provided through the coronary artery, the guidewire is advanced in one embodiment until the distal end 104 of the guidewire enters the left ventricle. Alternatively, where it is desired that a stent or other device extend only partially into the myocardium, the guidewire 100 need not extend all the way through to the left ventricle. The distal tip 104 of the guidewire 100 is preferably made of a radiopaque material that can be visualized by the physician by an available method, such as fluoroscopy.

The distal end of the guidewire 100 is preferably formed such that it is easily advanced but is difficult to pull back through the tissue. As shown in FIG. 17, one embodiment of the distal tip 104 comprises one or more barbs 106 extending from the tip in a type of "multi-winged arrowhead" configuration. These barbs allow the guidewire to be advanced distally into the myocardium but require more force to pull the guidewire 100 proximally out of the myocardium, thus creating an effective anchor.

Figure 18A:
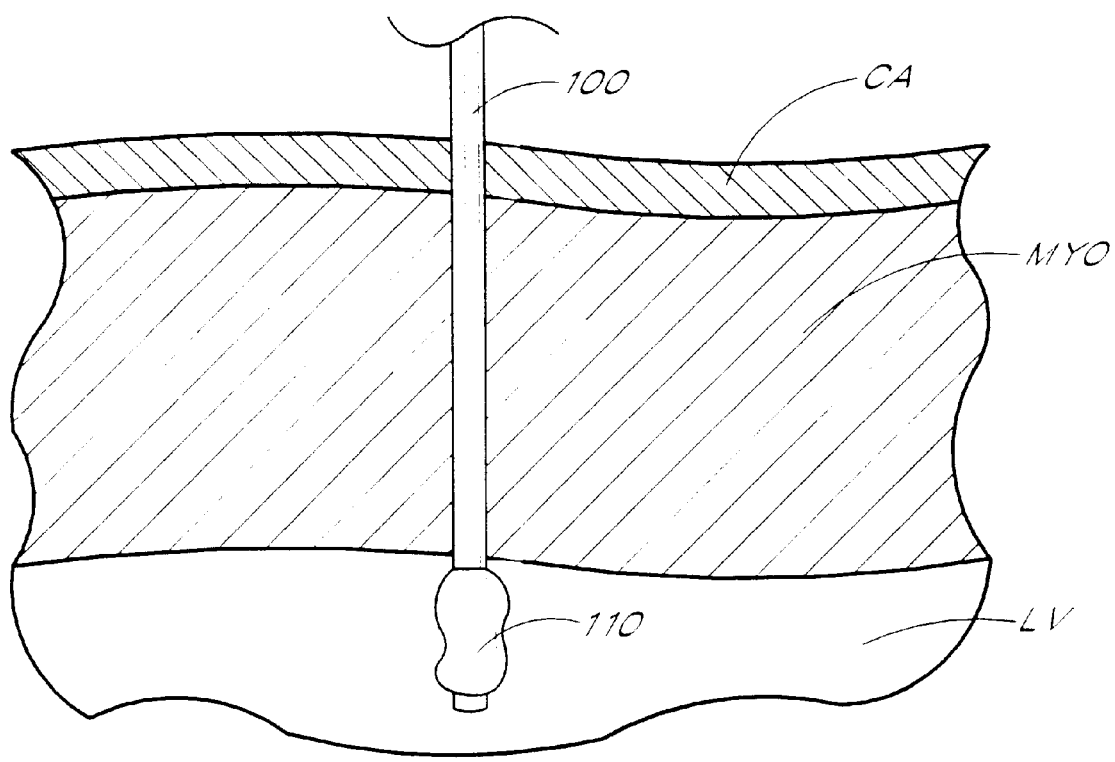
FIG. 18A is a side view of a guidewire carrying an inflatable balloon on its distal end extending through the myocardium, with the myocardium shown partially cut away.
Figure 18B:
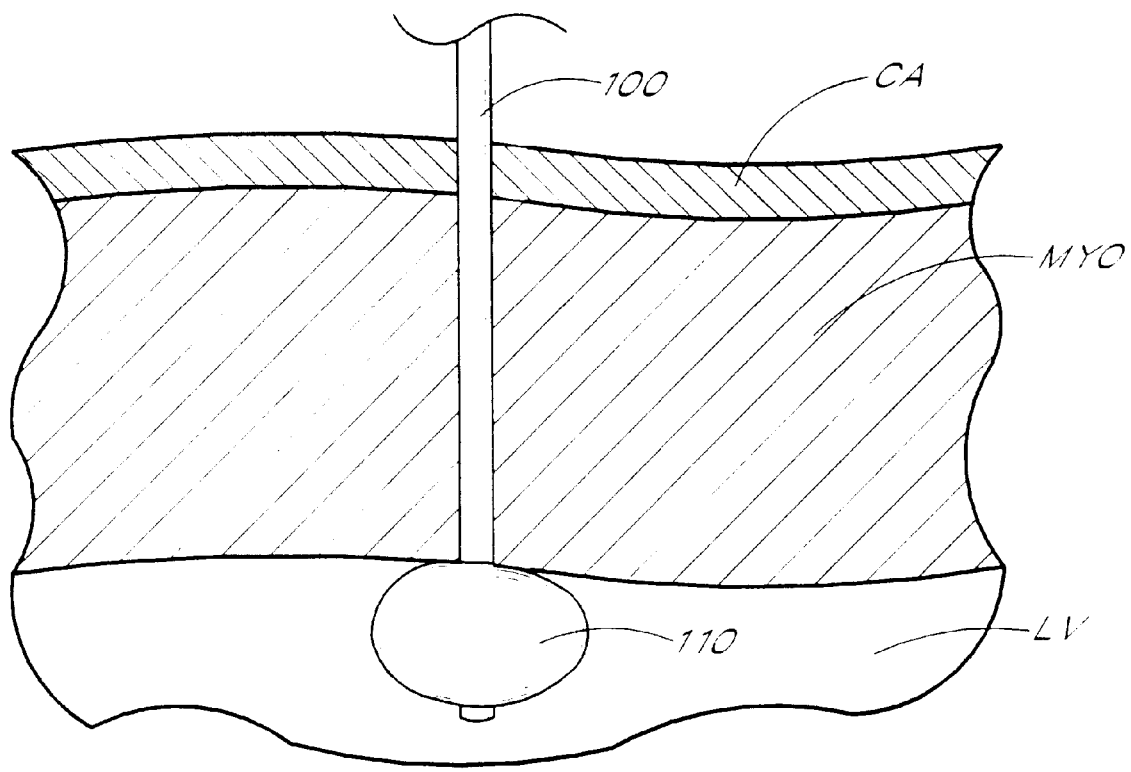
FIG. 18B is a side view of the guidewire of FIG. 18A, showing the balloon inflated to anchor the guidewire against the myocardium.

FIG. 18A shows another embodiment wherein a guidewire 100 carries an expandable member such as balloon 110 on its distal end. Use of an expandable member reduces damage to the myocardium during subsequent retraction of the wire 100. As illustrated in FIG. 18B, once the balloon 110 reaches the left ventricle LV, the balloon 110 is inflated. The balloon is then preferably pulled proximally back to the ventricle wall to anchor and secure the guidewire 100 in place.

Figure 19A:
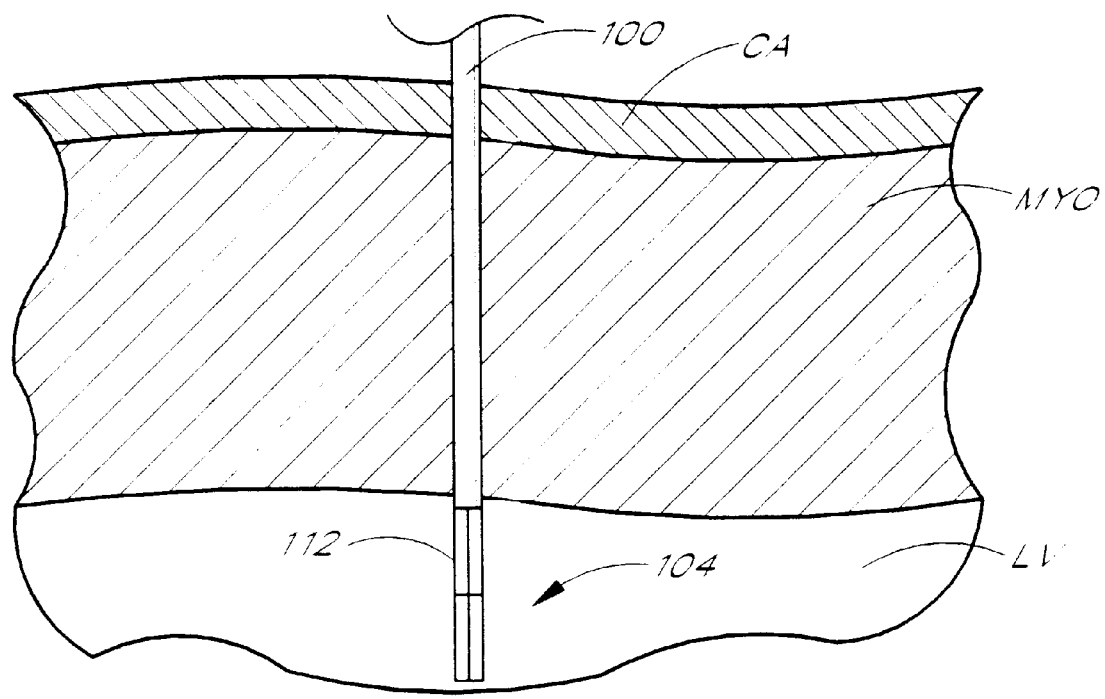
FIGS. 19A–19C are side views of an alternative embodiment of a guidewire anchored to the inner wall of the myocardium, with the myocardium shown partially cut away.
Figure 19B:
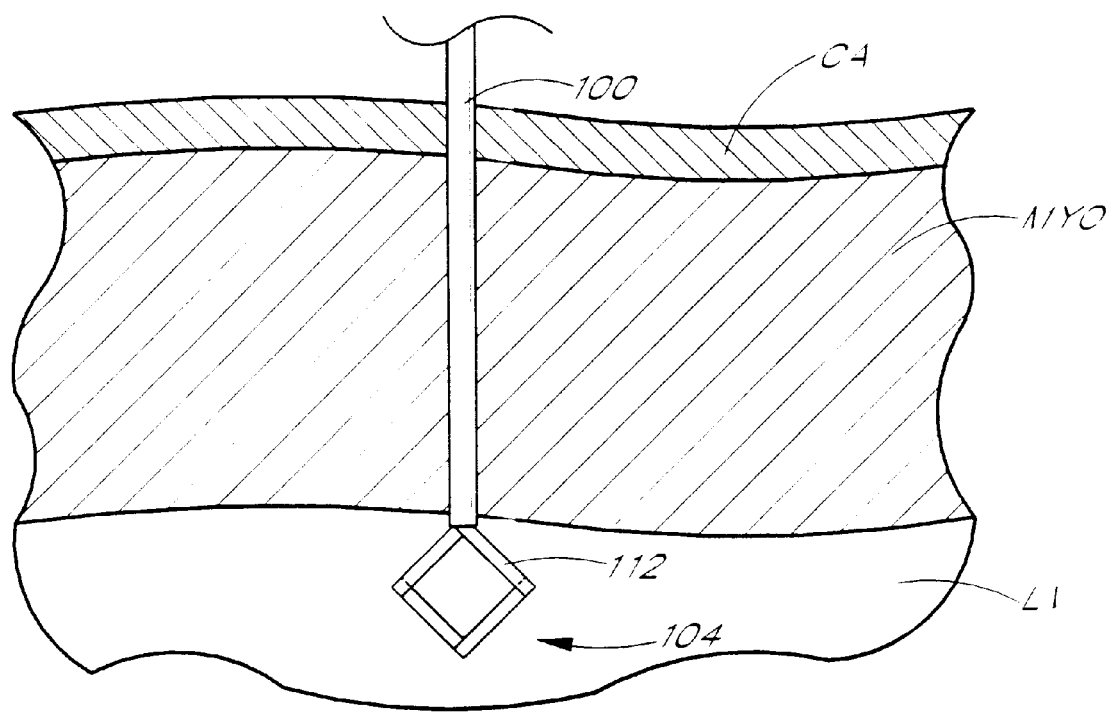
Figure 19C:
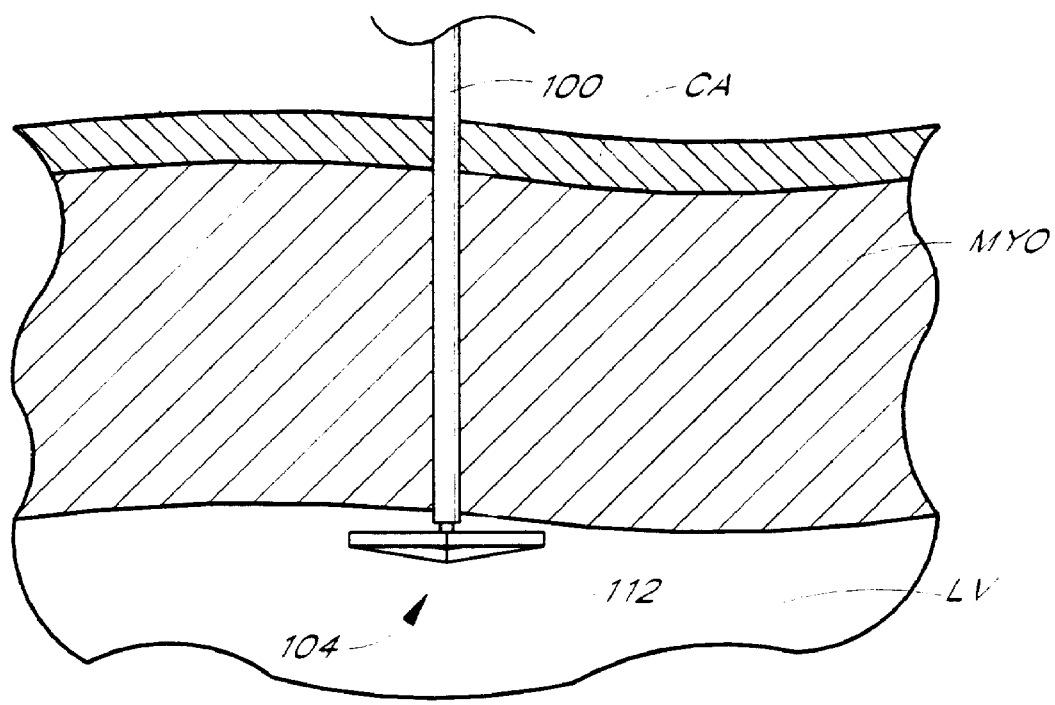

Alternatively, FIGS. 19A–19C show an expandable guidewire 100 extending through and actuated to anchor the guidewire within the myocardium MYO. In FIG. 19A, a guidewire 100 is shown advanced through the myocardium MYO. Guidewire 100 is provided with an expandable device 112 on distal end 104 which may be actuated by an operator at the proximal end of the guidewire outside of the patient. Actuating of the device may be accomplished by using a shape memory material such as nitinol and heating the material above its transformation temperature. Alternatively, the guidewire may be mechanically actuated to assume the desired shape. FIG. 19B shows the guidewire 100 partially actuated at its distal end 104 to expand the device 112 into an anchorable shape. FIG. 19C shows the expandable device 112 fully actuated to anchor the guidewire 100 against the ventricle wall. Other types of anchoring and expandable members may also be used to secure the guidewire 100.

Once the guidewire 100 is anchored in place, the delivery catheter may be removed without displacing the guidewire inserted through the myocardium. Then, with the guidewire 100 anchored in place, catheters used in creating and stenting the passageway or other medical devices may be provided into the myocardium. Alternatively, the delivery catheter may remain within the blood vessel and other catheters or medical devices may be advanced over the guidewire and through the delivery catheter. Furthermore, an expandable member such as a balloon may be provided on the delivery catheter or on the guidewire 100 to anchor the catheter or guidewire to the wall of the blood vessel to provide for more secure deployment of medical devices into the myocardium.

IV. Delivery Over the Guidewire

The anchoring of the guidewire 100 within the myocardium MYO allows for the delivery of devices into the myocardium for creation of a myocardial passageway. In particular, the anchoring of the guidewire 100 facilitates advancement of over-the-wire catheters such as introducer catheters into the myocardium by employing a push-pull mechanism. When it is desired to push a catheter over the guidewire 100, the guidewire 100 may be pulled proximally by an operator from outside of the body. The anchoring member at the distal end of the guidewire, whether a balloon, barb, or other member, prevents the guidewire 100 from exiting the myocardium MYO. Meanwhile, a delivery catheter or other over-the-wire device may be pushed into the myocardium MYO, assisted by the pulling force of the anchoring member toward the catheter. The anchoring member also assists in placement of an over-the-wire catheter in the myocardium by preventing the catheter from extending beyond the location of the anchoring member.

Figure 20:
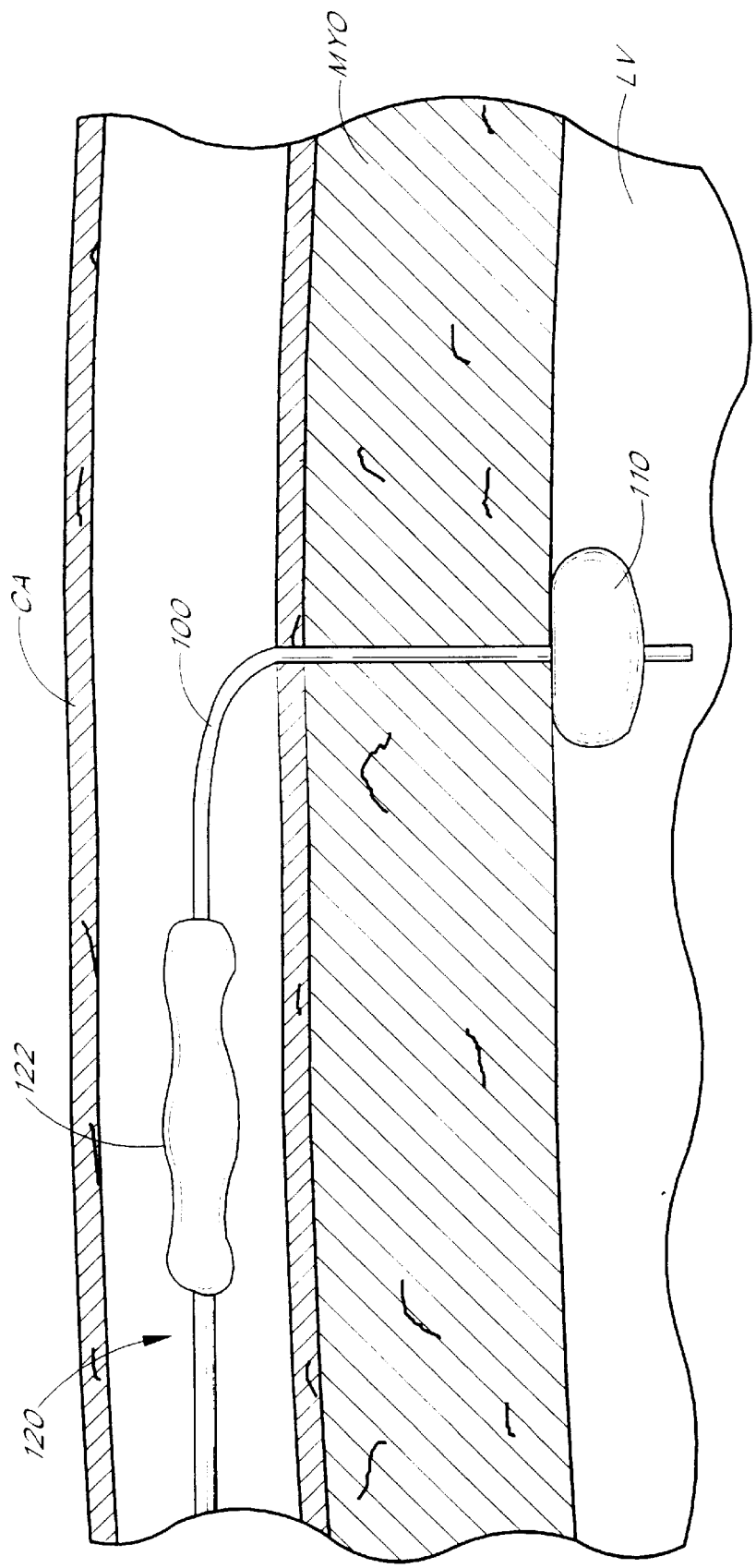
FIG. 20 is a side view of a dilation catheter in a coronary artery advanced over a guidewire extending into the myocardium, with the artery and the myocardium shown partially cut away.
Figure 21:
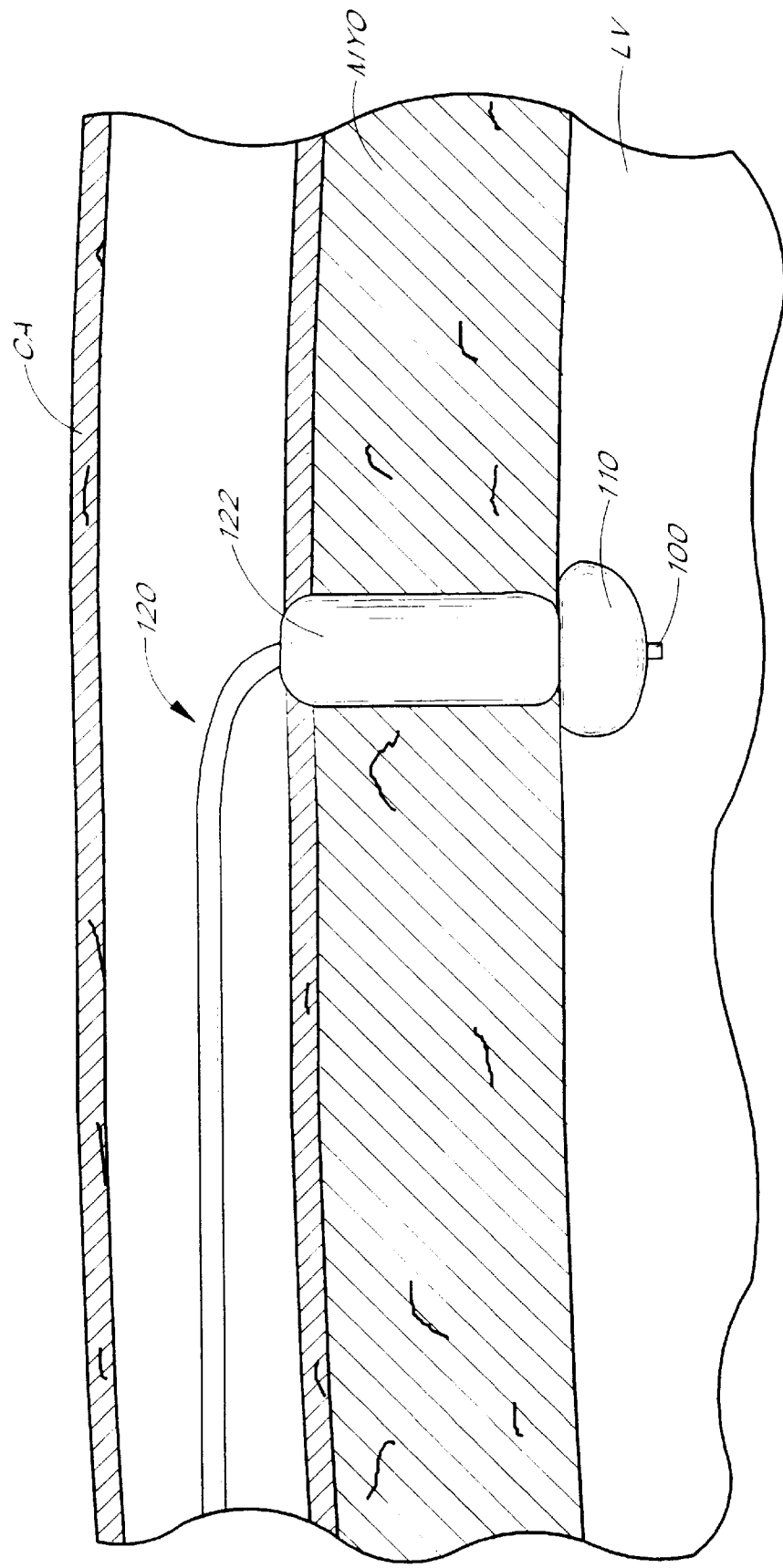
FIG. 21 is a side view of the dilation catheter of FIG. 20 advanced into the myocardium.

As illustrated in FIG. 20, to create a myocardial passageway, a catheter 120 having a dilation balloon 122 is advanced over guidewire 100, into the myocardium MYO, as shown in FIG. 21. The anchored balloon 110 acts as a barrier to advancement of balloon 122, which is subsequently inflated within myocardium MYO to expand a myocardial passageway. The balloon 122 is then deflated and the catheter 120 removed. The process may be repeated with successively larger dilation balloons to form a passageway of desired size.

Figure 22:
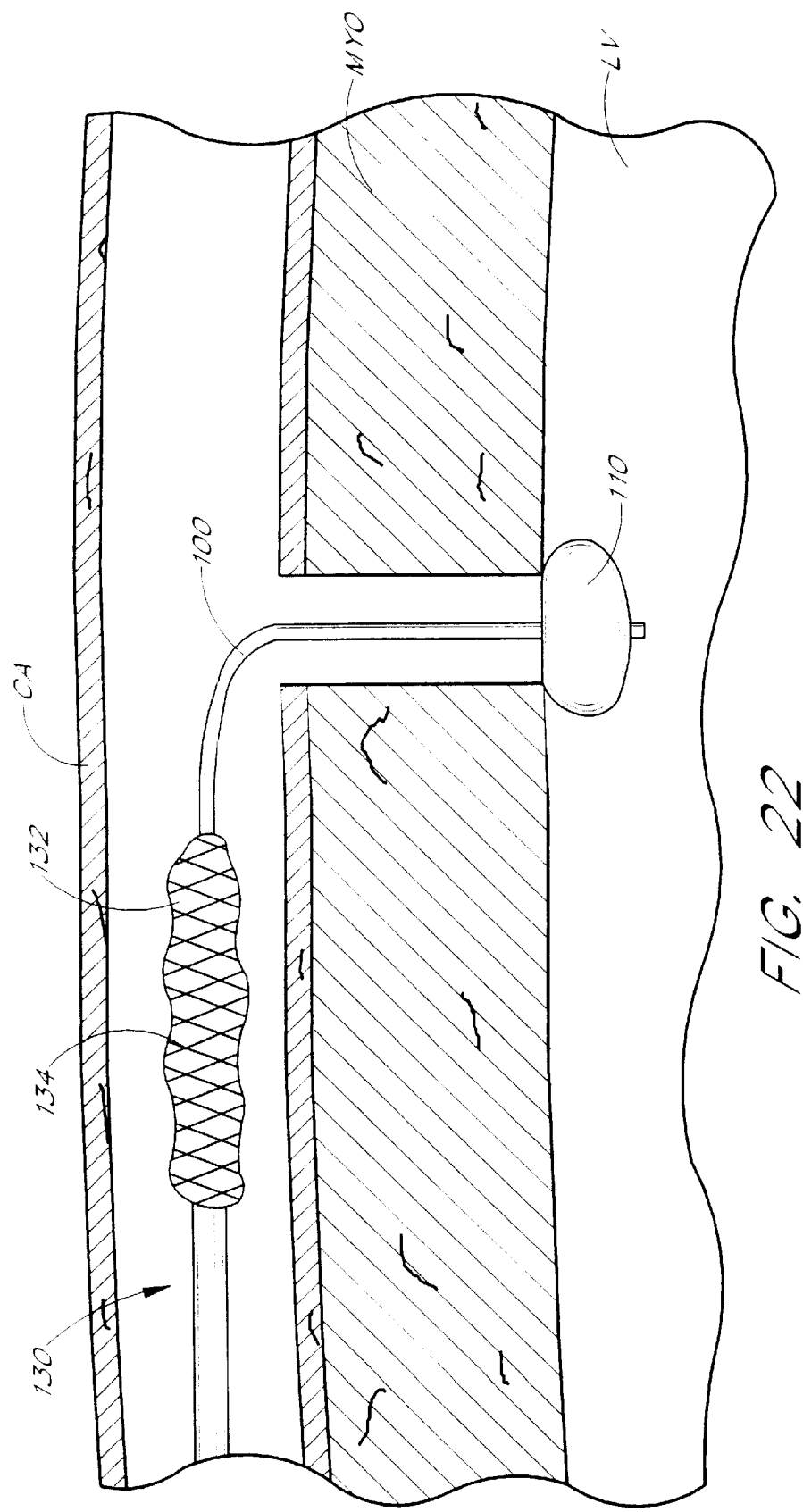
FIG. 22 is a side view of a stent introducer catheter in a coronary artery advanced over a guidewire extending into the myocardium, with the artery and myocardium shown partially cut away.
Figure 23:
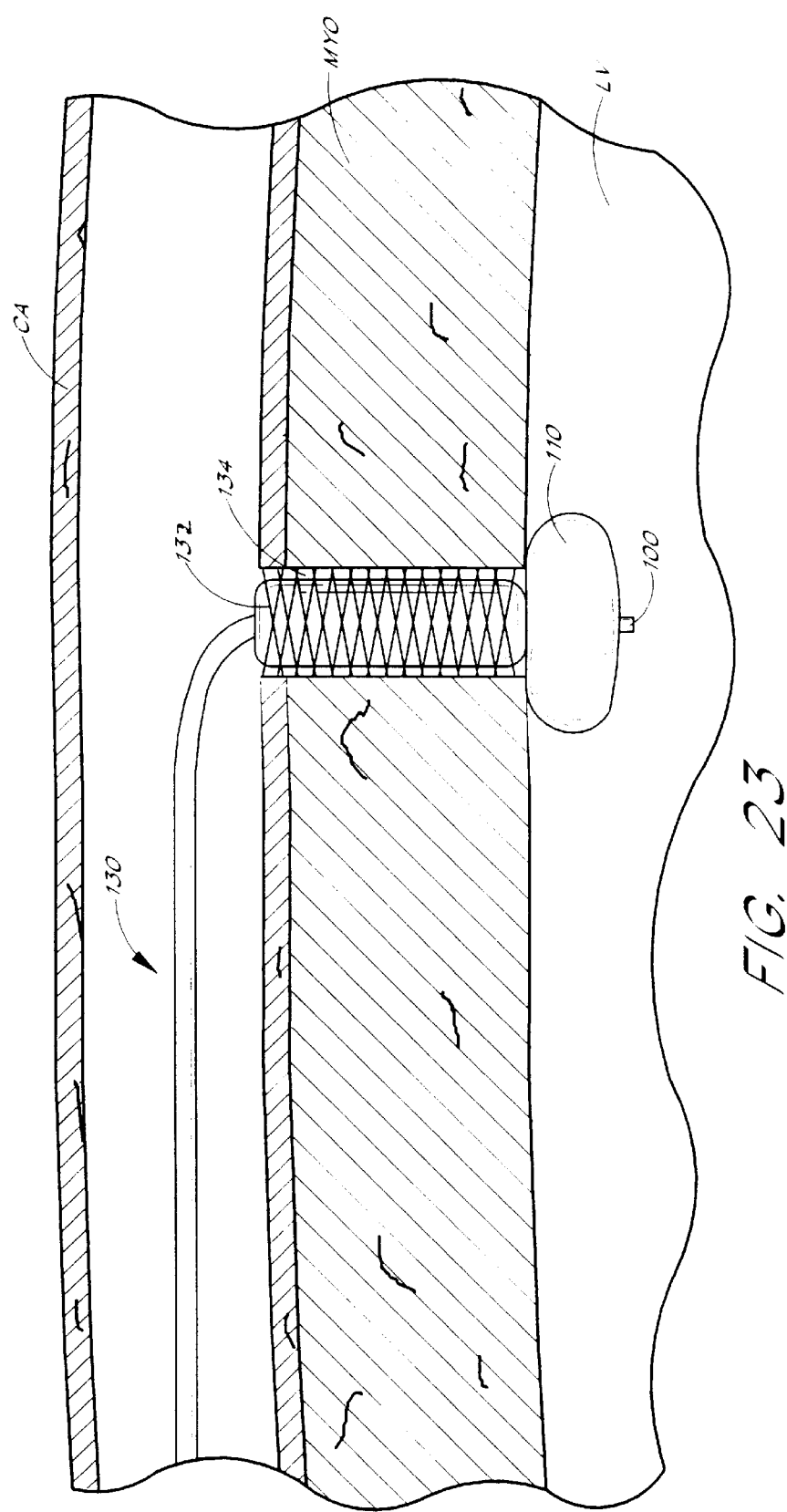
FIG. 23 is a side view of the stent introducer catheter of FIG. 22 advanced into the myocardium.

After inflation of the largest desired dilation balloon, the catheter 120 is withdrawn and a stent introducer catheter 130 is advanced over wire 100, as shown in FIG. 22. The catheter 130 has an inflatable balloon 132 mounted on its distal end for deploying a stent 134 carried by balloon 132. Upon the positioning of balloon 132 inside the myocardium MYO, balloon 132 is inflated, as shown in FIG. 23, to assist in an initial expansion of stent 134 in opposition to the compressive forces of the heart muscle. Upon the desired disposition of stent 134, balloon 132 is deflated and catheter 130 and wire 100 are withdrawn, leaving stent 134 in place to provide a coronary bypass between ventricle LV and artery CA.

V. Drug Delivery

Figure 24:
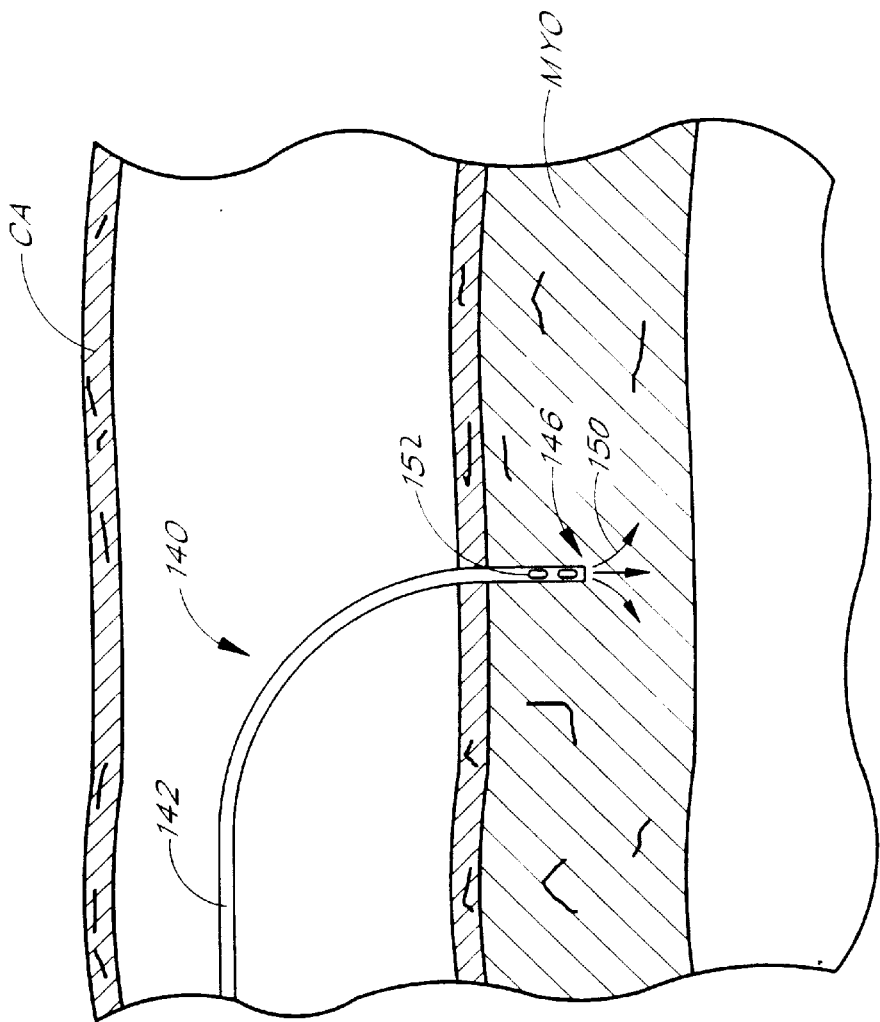
FIG. 24 is a side view of a drug delivery wire advanced through a coronary artery into the myocardium, with the artery and the myocardium shown partially cut away.

The guidewire such as described above delivered into the myocardium MYO may also be used for delivering drugs into the myocardium. As shown in FIG. 24, a guidewire 140 is advanced partially into the myocardium using any of the methods described above. The guidewire 140 comprises a tubular body 142 having a lumen 148 (not shown) extending from a proximal end 144 (not shown) to a distal end 146. The guidewire may be angled using the turning methods described above to provide the distal end of the guidewire at a desired position within the myocardium for drug delivery. Drug delivery fluids 150 are ejected from the distal and 146 into the myocardium. Although the guidewire 140 shown in FIG. 24 is not anchored to the myocardium MYO, anchoring means as described above may be provided. Furthermore, the guidewire 140 may contain a plurality of ports 152 along the tubular body 142 near the distal end 146.

The embodiments illustrated and described above are provided merely as examples of certain preferred embodiments of the present invention. Other changes and modifications can be made from the embodiments presented herein by those skilled in the art without departure from the spirit and scope of the invention, as defined by the appended claims.

What is claimed is:

1. A method for delivering a medical device into the myocardium of a patient, comprising:
    delivering a guidewire into the patient, the guidewire once delivered having a proximal end extending out of the patient and a distal end positioned adjacent the myocardium;
    inserting the distal end of the guidewire into the myocardium;
    creating a passage in the myocardium by expansion of an expandable member; and
    after creating the passage, advancing an introducer catheter carrying the medical device over the guidewire to deliver the device into the myocardium.

2. The method of claim 1, wherein the guidewire is delivered percutaneously into the patient.

3. The method of claim 2, wherein the distal end of the guidewire is advanced through a blockage in a coronary artery.

4. The method of claim 2, wherein the distal end of the guidewire is advanced through a coronary vein.

5. The method of claim 2, wherein the distal end of the guidewire is advanced into the left ventricle.

6. The method of claim 1, further comprising advancing a delivery catheter into the patient prior to delivering the guidewire, the delivery catheter comprising a tubular body having a proximal end and a distal end and a lumen extending at least partially therethrough, until the distal end of the delivery catheter is positioned adjacent the myocardium.

7. The method of claim 6, further comprising turning the distal end of the guidewire toward the myocardium prior to inserting the distal end of the guidewire, by:
    actuating an anchoring member mounted on the distal end of the delivery catheter to secure the delivery catheter within the patient; and
    actuating a steering member mounted on the distal end of the tubular body at a position distal to that of the anchoring member to turn the distal end of the delivery catheter toward the myocardium; and
    advancing the guidewire through the lumen in the delivery catheter and out the distal end of the delivery catheter.

8. The method of claim 1, wherein the guidewire is a tip-deflecting wire, and further comprising turning the distal end of the guidewire toward the myocardium prior to inserting the distal end of the guidewire by actuating the tip-deflecting wire.

9. The method of claim 1, further comprising:
    providing a passageway adjacent the myocardium having a proximal opening for receiving the distal end of the guidewire and a side port exit facing the myocardium;
    wherein delivering the guidewire comprises advancing the distal end of the guidewire through the passageway toward the myocardium.

10. The method of claim 9, wherein the passageway is provided through a lumen in a delivery catheter.

11. The method of claim 9, wherein the passageway is provided through an anchoring member mounted to a distal end of a delivery catheter.

12. The method of claim 1, further comprising anchoring the guidewire to the myocardium.

13. The method of claim 12, wherein anchoring the guidewire to the myocardium comprises providing at least one barb attached to the distal end of the guidewire, the barb having a shape that facilitates advancement of the guidewire distally through the myocardium but prevents retraction of the guidewire proximally.

14. The method of claim 1, wherein inserting the distal end of the guidewire into the myocardium comprises advancing the guidewire from a coronary blood vessel until the distal end extends into the left ventricle.

15. The method of claim 12, wherein anchoring the guidewire further comprises expanding an anchoring member mounted on the distal end of the guidewire within the left ventricle.

16. The method of claim 15, wherein the anchoring member is an inflatable balloon.

17. The method of claim 12, wherein advancing the introducer catheter carrying a medical device further comprises: member into the aneurysm.

18. The method of claim 1, wherein the step of creating a passage includes advancing a second introducer catheter into the myocardium.

19. The method of claim 1, wherein the expandable member is inflatable.

20. The method fo claim 19, wherein the expandable member is a balloon.

21. A method for delivering a medical device into a body tissue of a patient comprising:

inserting a guidewire having a proximal end and a distal end into the myocardium from a coronary blood vessel;

anchoring the guidewire to the body tissue;

pushing the medical device over the guidewire into the body tissue; and pulling on the proximal end of the guidewire while advancing the medical device through the body tissue.

22. The method of claim 21, wherein anchoring the guidewire comprises actuating an expandable member.

23. The method of claim 22, wherein the expandable member is an inflatable balloon.

24. The method of claim 21, further comprising providing at least one barb on the distal end of the guidewire to anchor the guidewire to the myocardium.

25. A method for delivering a stent into the myocardium of a patient to bypass a blockage formed in a coronary artery, comprising:

advancing a catheter having a proximal end and a distal end and a lumen extending at least partially therethrough from the proximal end to a distal opening through the coronary artery of the patient until the distal opening is past the blockage;

turning the catheter so that the distal opening faces the myocardium;

extending a wire having a proximal end and a distal end through the distal opening such that the distal end punctures into the myocardium;

anchoring the distal end of the wire to the myocardium;

delivering a dilation catheter over the wire, the catheter carrying a dilation balloon on a distal end thereof, until the balloon is within the myocardium;

inflating the dilation balloon to create an opening in the myocardium;

deflating the dilation balloon and removing the dilation catheter from the wire;

delivering a stent introducer catheter over the wire, the stent introducer catheter carrying a stent on a distal end thereof, until the stent is located within the opening in the myocardium, and deploying the stent within the opening in the myocardium.

26. A method for creating a passage defined by a heart wall, comprising:

inserting a guidewire through the heart wall such that a portion of the guidewire rests in the heart wall;

positioning an expandable member over the portion of the guidewire in the heart wall;

expanding the expandable member within the heart wall to form the passage in the heart wall;

removing the expandable member from the heart wall; and after removal of the expandable member, delivering a stent to the passage formed in the heart wall.

27. The method of claim 26, wherein positioning the expandable member includes disposing the expandable member on a catheter and advancing the catheter over the guidewire until the expandable member is over the portion of the guidewire in the heart wall.

28. The method of claim 26, wherein prior to inserting the guidewire through the heart wall, a distal end of the guidewire penetrates a wall of a coronary vessel.

29. The method of claim 28, wherein the coronary vessel is a coronary artery and the distal end of the guidewire penetrates the posterior wall of the coronary artery.

30. The method of claim 29, wherein the guidewire enters the coronary vessel percutaneously.

31. The method of claim 26, wherein the stent is configured to have a diameter such that the stent lies flush with the passage.

32. The method of claim 31, wherein delivering the expandable member includes advancing a first catheter over the guidewire, the expandable member being disposed on the first catheter, and wherein delivering the stent includes advancing a second catheter over the guidewire, the stent being disposed on the second catheter.

33. The method of claim 31, wherein delivering the stent includes delivering the stent in a collapsed configuration to the passage formed in the heart wall and expanding the stent in the passage so that the stent lies flush with the passage.

34. The method of claim 33, wherein expanding the stent includes providing a second expandable member which carries the stent during delivery to the passage and expanding the second expandable member in the passage to thereby expand the stent.

35. The method of claim 34, wherein expanding the expandable members includes inflating the expandable members.

36. The method of claim 33, wherein delivering the stent includes disposing the stent on a catheter and advancing the catheter over the guidewire and into the passage.

37. The method of claim 26, wherein the passage connects the left ventricle to the coronary artery.

38. The method of claim 26, wherein the expandable member and the stent are on separate catheters.

* * * * *

UNITED STATES PATENT AND TRADEMARK OFFICE
CERTIFICATE OF CORRECTION

PATENT NO. : 6,196,230 B1
DATED : March 6, 2001
INVENTOR(S) : Scott J. Wolf et al.

It is certified that error appears in the above-identified patent and that said Letters Patent is hereby corrected as shown below:

Title page,
Item [75], Inventors, lines 1-3, delete "Todd A. Hall, Goshen; Greg R. Furnish; Simon M. Furnish, both of Louisville, all of KY (US);" and
Lines 5-6, delete "David Y. Phelps, Louisville, KY (US);"

Column 15, claim 17,
Line 25, replace "member into the aneurysm." with -- pulling proximally on the guidewire anchored to the myocardium; and pushing the introducer catheter over the guidewire into the myocardium. --

Column 15, claim 20,
Line 30, replace "method fo" with -- method of --.

Signed and Sealed this

Twenty-fifth Day of December, 2001

*Attest:*

JAMES E. ROGAN
*Attesting Officer*     *Director of the United States Patent and Trademark Office*